US011660223B1

(12) United States Patent
Alhawsawi

(10) Patent No.: US 11,660,223 B1
(45) Date of Patent: May 30, 2023

(54) SMART KNEE BRACE FOR POST-SURGERY REHABILITATION

(71) Applicant: King Abdulaziz University, Jeddah (SA)

(72) Inventor: Abdulsalam M. Alhawsawi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/583,484

(22) Filed: Jan. 25, 2022

(51) Int. Cl.
| | | |
|---|---|---|
| *A61F 5/01* | (2006.01) | |
| *A61H 1/02* | (2006.01) | |
| *B25J 13/08* | (2006.01) | |
| *B25J 9/00* | (2006.01) | |

(52) U.S. Cl.
CPC ........... *A61F 5/0123* (2013.01); *A61H 1/024* (2013.01); *B25J 9/0006* (2013.01); *B25J 13/088* (2013.01); *A61H 2201/0207* (2013.01); *A61H 2201/0214* (2013.01); *A61H 2201/1207* (2013.01); *A61H 2201/1238* (2013.01); *A61H 2201/165* (2013.01); *A61H 2201/1642* (2013.01); *A61H 2201/1664* (2013.01); *A61H 2201/5007* (2013.01); *A61H 2201/5048* (2013.01); *A61H 2201/5082* (2013.01)

(58) Field of Classification Search
CPC ..... A61H 1/024; A61F 5/0123; A61F 5/0125; A61F 2007/0042; B25J 9/0006; B25J 13/08
See application file for complete search history.

(56) References Cited

U.S. PATENT DOCUMENTS 5,277,697 A * 1/1994 France ................. A61F 13/062
602/26
5,472,412 A 12/1995 Knoth
(Continued)

FOREIGN PATENT DOCUMENTS

| CN | 10439481 B | 4/2017 |
| IN | 20110331914 | 11/2012 |

OTHER PUBLICATIONS

Darwin Gouwanda, et al., "A Robust Real-time Gait Event Detection using Wireless Gyroscope and Its Application on Normal and Altered Gaits", Medical Engineering and Physics, vol. 37, No. 2, Feb. 2015, pp. 1-25.

*Primary Examiner* — Timothy A Stanis
(74) *Attorney, Agent, or Firm* — Oblon, McClelland, Maier & Neustadt, L.L.P.

(57) ABSTRACT

A smart knee brace including a knee brace, multiple thigh bands, multiple shin bands, and multiple brace straps removably attached to one another and multiple motion actuators and sensors. Each motion actuator is connected to one brace strap and each sensor is connected to one motion actuator to measure an orientation of corresponding brace strap and generate a motion signal. A computing device receives the motion signals from the sensors; measures a current range of motion of the thigh, the shin, and the knee, and, based on the received motion signals, and generates drive signals based on the measured current range of motion. A native smart knee brace computer application on a smart phone of the user is operatively connected to the computing device and a cloud application server provide higher level analysis of the motions of the smart knee brace.

18 Claims, 16 Drawing Sheets

(56) References Cited

U.S. PATENT DOCUMENTS

| | | | |
|---|---|---|---|
| 6,551,264 B1* | 4/2003 | Cawley | A61F 5/0125 |
| | | | 128/882 |
| 7,513,881 B1* | 4/2009 | Grim | A61F 5/0585 |
| | | | 602/5 |
| 7,883,479 B1 | 2/2011 | Stanley et al. | |
| 9,295,575 B1* | 3/2016 | Dignam | A61F 5/0102 |
| 10,932,939 B1* | 3/2021 | Pahls | A61F 5/0123 |
| 2008/0066272 A1* | 3/2008 | Hammerslag | A43C 11/14 |
| | | | 602/5 |
| 2008/0249448 A1* | 10/2008 | Stevenson | A61F 5/0125 |
| | | | 602/5 |
| 2013/0245523 A1* | 9/2013 | Romo | A61F 5/0125 |
| | | | 602/16 |
| 2014/0303534 A1* | 10/2014 | Huffa | A61F 5/0102 |
| | | | 602/6 |
| 2015/0150705 A1* | 6/2015 | Capra | A61F 5/0123 |
| | | | 602/6 |
| 2015/0328032 A1* | 11/2015 | Walker | A61F 5/0109 |
| | | | 602/26 |
| 2016/0220175 A1 | 8/2016 | Tam et al. | |
| 2016/0242646 A1* | 8/2016 | Obma | A61B 5/1114 |
| 2016/0371997 A1* | 12/2016 | Angerer | A61N 1/38 |
| 2017/0087000 A1* | 3/2017 | Cain | A61F 5/0127 |
| 2017/0151083 A1* | 6/2017 | Lee | A61F 5/0104 |
| 2017/0360586 A1* | 12/2017 | Dempers | A61F 5/0109 |
| 2018/0256381 A1* | 9/2018 | Chang | A61F 5/048 |
| 2020/0155342 A1 | 5/2020 | Schultz | |
| 2020/0179216 A1* | 6/2020 | Choi | A61H 1/024 |
| 2020/0253815 A1* | 8/2020 | Berry | A61H 23/02 |

\* cited by examiner

SMART KNEE BRACE FOR POST-SURGERY REHABILITATION

STATEMENT OF ACKNOWLEDGEMENT

The inventor(s) acknowledge the financial support provided by the Knowledge Economy & Technology Transfer Center, King Abdulaziz University, Jeddah, Saudi Arabia through grant number 2020-012.

BACKGROUND

Technical Field

The present disclosure is directed to a knee brace system that can be placed in a first configuration to immobilize the knee post surgery and in a second configuration to move the knee during rehabilitation.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

During therapeutic treatment of the knee which includes surgery and joint replacement, it is often required to stabilize the knee to impart medial and lateral stability for a period of time during the healing process. A variety of adjustable knee braces are available through healthcare providers to be worn over or under clothing, to protect and strengthen areas subjected to the surgery and joint replacement. The knee braces range from those that totally immobilize the knee to flexible elastic bandages that are intended to provide some flexibility while eliminating lateral movement of the ligaments that support the knee. These knee braces may be worn as a permanent device for long-term wear or for a short duration during rehabilitations sessions or as an aid in supporting the knee during healing.

Typically, after an orthopedic knee surgery, patients use a continuous passive motion machine to mobilize the joint immediately after the surgery. Alternatively, the patient may wear a large knee brace to limit movement of the knee joint, depending on the extent of the surgery. However, the large knee brace may need to be removed prior to physical therapy sessions. During the physical therapy sessions, the patient may need to wear a different knee brace to perform suggested exercises and stabilize the knee. As such, the patient is required to change the knee brace during the physical therapy session and after the physical therapy session, which may be inconvenient and time consuming for the patient and the physical therapist. Known knee braces includes hinges that are disposed on either sides of the leg to mimic action of the knee joint. However, such knee braces fail to immobilize the knee joint in cases where it is required to limit the movement of the knee joint.

IN20110331914 describes a method of controlling knee movement, through a knee brace, by sensing movement via motion sensors, force sensors, and angle detectors disposed within the knee brace. CN104394810B describes adjustable and conforming post-operative knee braces having a flexible strap fixed on a first support and a second support. U.S. Pat. No. 5,472,412A describes articulated knee brace having a pair of arms pivotally connected pivot pins and gear segments. Each of these references is herein incorporated in its entirety. However, adjusting a resistance to flexion and extension of the knee brace and the limb in this reference is achieved by flow of hydraulic fluid through valves and piston chambers to pivot the arms. None of these patents mention a controller configured to immobilize or control the knee movement based on prescribed physical therapy instructions, or that the same knee brace can be used for immobilization of the knee as well as during rehabilitation sessions.

Each of the aforementioned references suffers from one or more drawbacks hindering their adoption. Accordingly, it is one object of the present disclosure to provide a smart knee brace which can be configured for immobilizing a knee and for movement of the knee during rehabilitation, where the movement is sensed and performed under computer control.

SUMMARY

In an exemplary embodiment, a smart knee brace system is disclosed. The smart knee brace system includes a knee brace configured to wrap around and support a knee of a human patient; a plurality of thigh bands; a plurality of shin bands; a plurality of adjustable brace straps configured to removably attach to one or more of the knee brace, the thigh bands, and the shin bands. Each thigh band is configured to wrap around a thigh and each shin band is configured to wrap around a shin of the human patient. The smart knee brace system further includes a plurality of motion actuators and a plurality of sensors, where each sensor connected to one of plurality of the motion actuators. Each motion actuator is configured to be connected to one of the plurality of adjustable brace straps and each sensor is configured to measure an orientation of a corresponding adjustable brace strap and generate a motion signal. The smart knee brace system also includes a computing device having a circuitry including a communications device, and program instructions stored therein. The program instructions when executed by one or more processors, cause the one or more processors to receive the motion signals from the plurality of sensors; measure a current range of motion of the thigh, the shin, and the knee, based on the received motion signals; generate drive signals based on the measured current range of motion; and transmit the drive signals to each of the plurality of motion actuators.

In another exemplary embodiment, a method for immobilizing a knee with a smart knee brace system is disclosed. The method includes wrapping a knee brace around a knee, a first portion of a thigh and a second portion of a shin of a human patient; wrapping one or more thigh bands around the first portion; wrapping one or more shin bands around the second portion; attaching one or more brace straps between the one or more thigh bands and the knee brace, the one or more shin bands and the knee brace, and the one or more thigh bands and the one or more shin bands. The method further includes attaching one or more motion actuators to the one or more brace straps; and generating, by a computing device having circuitry including a communications device, a memory storing program instructions for knee immobilization, and one or more processors, configured to perform the program instructions, drive signals configured to one of extend or retract the one or more motion actuators in accordance with the program instructions for knee immobilization.

In yet another exemplary embodiment, a method of performing physical therapy with a smart knee brace system is disclosed. The method includes wrapping a knee brace around a knee, a first portion of a thigh and a second portion of a shin of a human patient; wrapping a first subset of a plurality of thigh bands around the first portion; wrapping a second subset of the plurality of thigh bands around the thigh above the first portion; wrapping a third subset of a plurality of shin bands around the second portion; and wrapping a fourth subset of the plurality of shin bands around the shin below the second portion. The method further includes attaching one or more brace straps between at least one of the first subset and the knee brace, the second subset and the knee brace, the first subset and the second subset, the third subset and the knee brace, the fourth subset and the knee brace, and the third subset and the fourth subset; and attaching one or more motion actuators to the one or more brace straps. The method also includes receiving, by a computing device having circuitry including a communications device, a memory storing a current set of physical therapy instructions, and one or more processors configured to perform the current set of physical therapy instructions, motion signals from one or more sensors connected with the one or more motion actuators; measuring a current range of motion of the thigh, the shin, and the knee; generating drive signals; actuating the one or more motion actuators in accordance with drive signals based on the current set of physical therapy instructions; and transmitting data associated with the current range of motion to a computer application.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
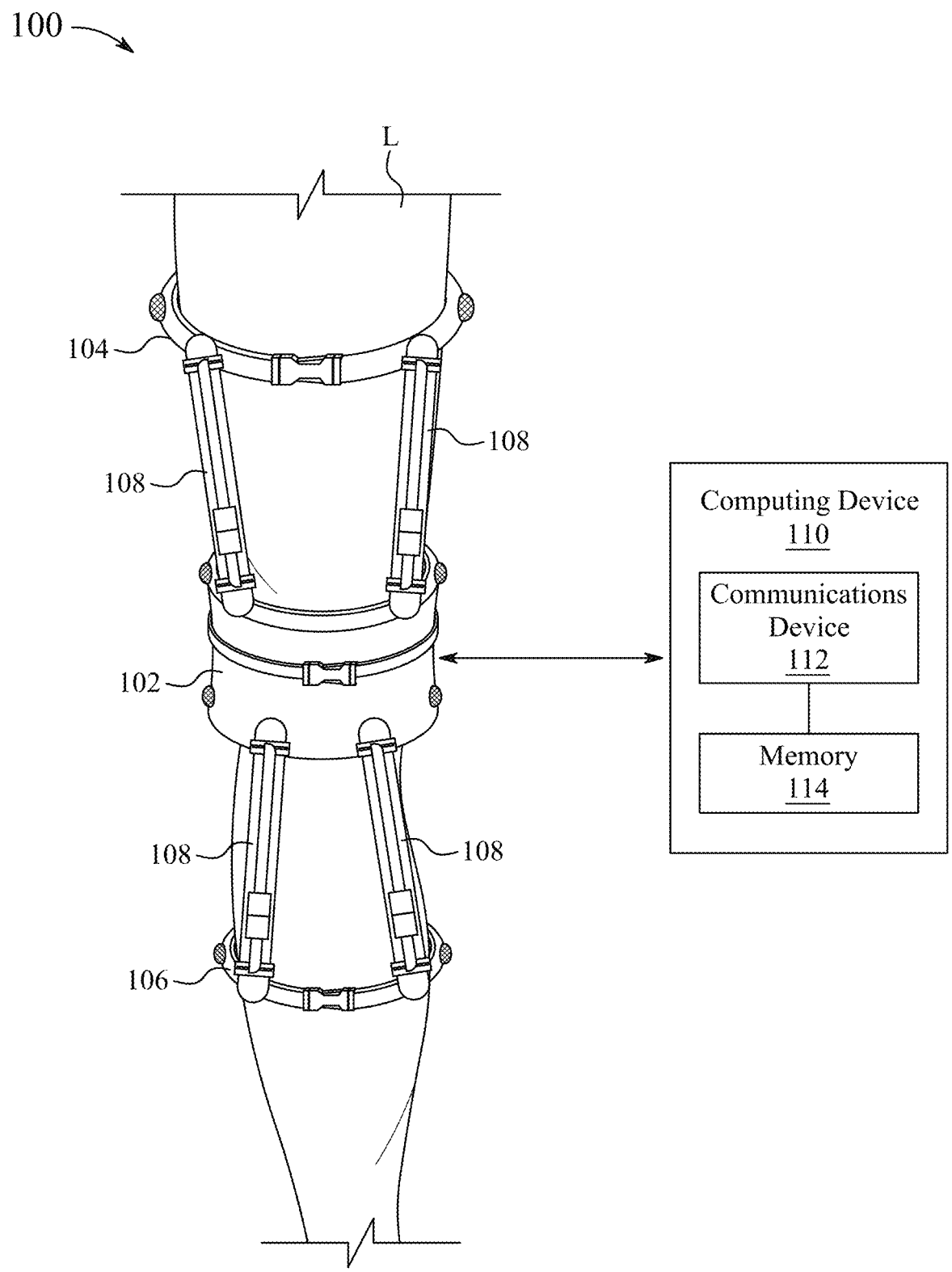
FIG. 1 is an exemplary view of a smart knee brace system installed on a leg of a patient, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a smart knee brace system and methods for immobilizing a knee of a human patient and assisting in performing physical therapy. The smart knee brace system replaces a continuous passive motion machine (CPM), stabilization braces, and physical therapy braces and combines them into one knee brace with multiple pieces that can be assembled and disassembled. Further, aspects of the present disclosure may be adapted and implemented to heal injuries caused to arm, shoulder, elbow, hip, lower back/vertebra.

FIG. 1 illustrates a smart knee brace system 100 (hereinafter referred to as "the system 100") installed on a leg "L" of a human patient. The system 100 includes a knee brace 102, a plurality of thigh bands and a plurality of shin bands. Among the plurality of thigh bands, one thigh band 104 is shown and, among the plurality of shin bands, one shin band 106 is shown for purpose of brevity. In a non-limiting example, each of the knee brace 102, the thigh band 104, and the shin band 106 may be made of neoprene or an elastic knitted fabric. The system 100 includes a plurality of adjustable brace straps 108 configured to removably attach to one or more of the knee brace 102, the thigh band 104, and the shin band 106. Each of these components of the system 100 may individually be worn by the patient on the leg "L", and hence allows for easy assembly and dismantle of the system 100. The knee brace 102 may have a central hole (see FIG. 3C) to accommodate the knee without compressing it. The knee brace 102 may be used during the first phase of healing and also during later physical therapy sessions, with different configurations of thigh bands. The knee brace may be installed and removed by releasing attachments or VELCRO™ fasteners. Alternatively, during physical therapy sessions, the knee brace 102 may be removed and only the shin band 106 and thigh band 104 may be used, as shown in FIG. 3E.

In a non-limiting example, knee brace, shin band and thigh band may be made of may be made from neoprene or an elastic knitted fabric. The neoprene or elastic knitted fabric may be formed as pockets filled with foam. In another non-limiting example, the knee brace may be made of a hard leather. The inner surface which contacts the leg and knee may be laminated to soft foam material covered with fabric. In another non-limiting example, the knee brace may be made all or partially from plastic.

Figure 2A:
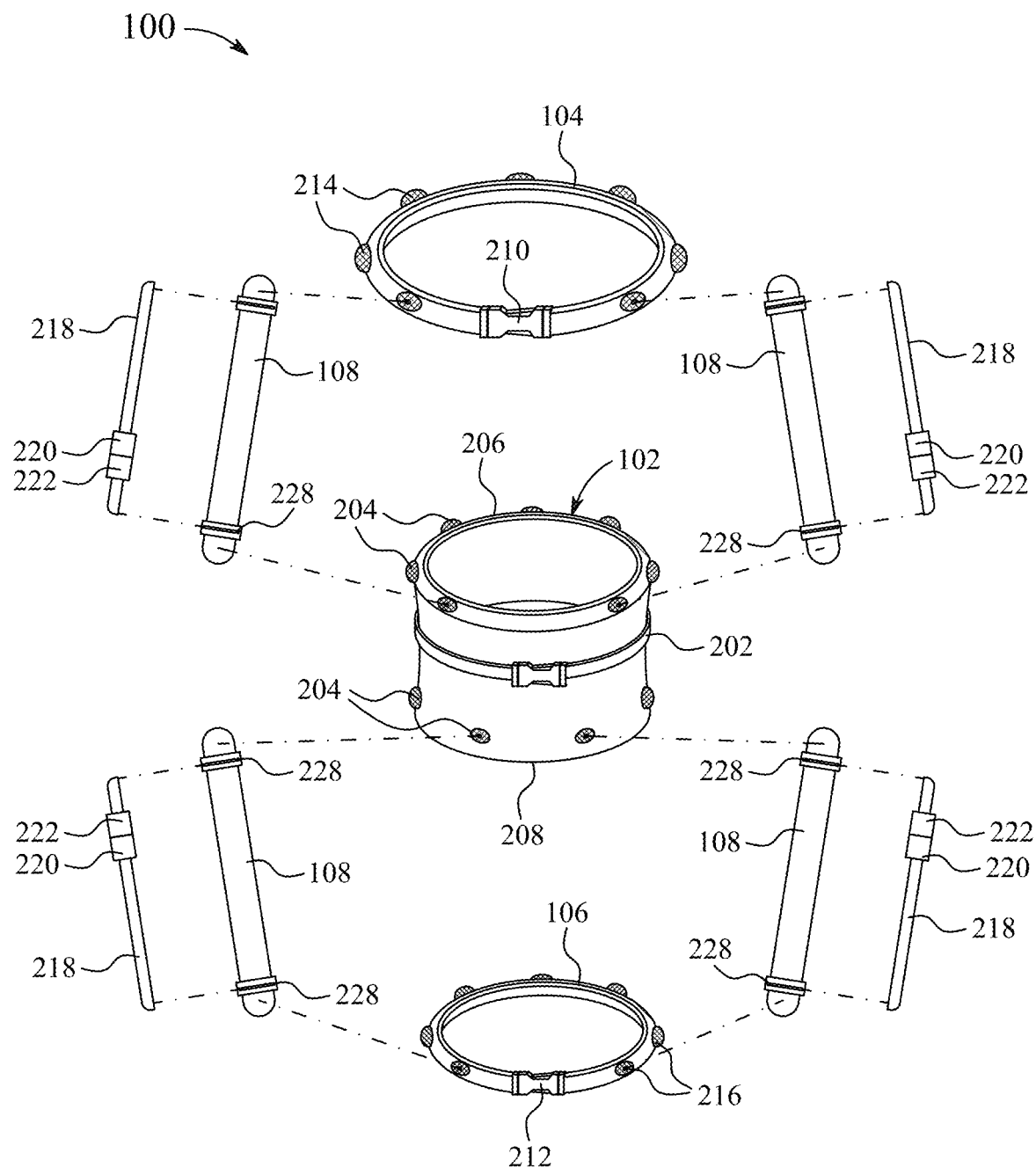
FIG. 2A is an exploded view of the smart knee brace system of FIG. 1, according to certain embodiments.

An exploded view of the system 100 is illustrated in FIG. 2A. The knee brace 102 is configured to wrap around and support a knee of the patient. In an aspect, the knee brace 102 includes a cutout (not shown) to accommodate the knee. The knee brace 102 may include, for example, a first strap 202 that extends along a periphery thereof, to rigidly secure the knee brace 102 around the knee. In a non-limiting example, the first strap 202 may include a buckle clip to secure the knee brace 102 around the knee. Other securing means, such as a Velcro®, known to a person skilled in the art may be used. Further, the knee brace 102 defines a first set of attachments 204 at a first end 206 and a second end 208 thereof. In an example, each attachment of the first set of attachments 204 may be a female part of a metal snap fastener. In other examples, each attachment may be a rear-earth magnet, such as a neodymium magnet.

Each of the thigh band 104 and the shin band 106 may be embodied as a flexible band. The thigh band 104 is configured to wrap around a thigh of the patient and the shin band 106 is configured to wrap around a shin of the patient. In an aspect, the flexible band may include a coupling at ends thereof to achieve a joint. In a non-limiting example, the coupling may be one of a buckle clip, a metal snap fastener, or a Velcro®. In another aspect, the thigh band 104 and the shin band 106 may include a second strap 210 and a third strap 212 extending along respective peripheries thereof to rigidly secure the thigh band 104 and the shin band 106 on the leg "L". In one aspect, each of the thigh band 104 and the shin band 106 may include a marking, such as a word "thigh", to indicate it as the thigh band 104. In cases where the patient has access to the plurality of thigh bands and the plurality of shin bands, such markings may help the patient to easily distinguish the bands.

Further, the thigh band 104 defines a second set of attachments 214 at an outer periphery thereof, and the shin band 106 defines a third set of attachments 216 at an outer periphery thereof as shown in FIG. 2A. Respective inner peripheries of the thigh band 104 and the shin band 106, that is configured to abut the leg "L", may include a soft material to provide comfort to the patient.

The system 100 further includes a plurality of motion actuators 218. Each motion actuator 218 is configured to be connected to one of the plurality of adjustable brace straps 108 as illustrated in FIG. 1. In one non-limiting example, each motion actuator 218 may be a bi-directional linear actuator. In another non-limiting example, the plurality of motion actuators 218 may include at least one of a hydraulic actuator and an electronic actuator. In an aspect, each motion actuator 218 includes a motor 220. Upon receipt of an input signal, each motion actuator 218 may be configured to expand or retract. The system 100 further includes a plurality of sensors 222. Each sensor 222 is connected to one of the plurality of the motion actuators 218 and configured to: (a) measure an orientation of a corresponding adjustable brace strap 108 and (b) generate a motion signal.

Figure 2B:
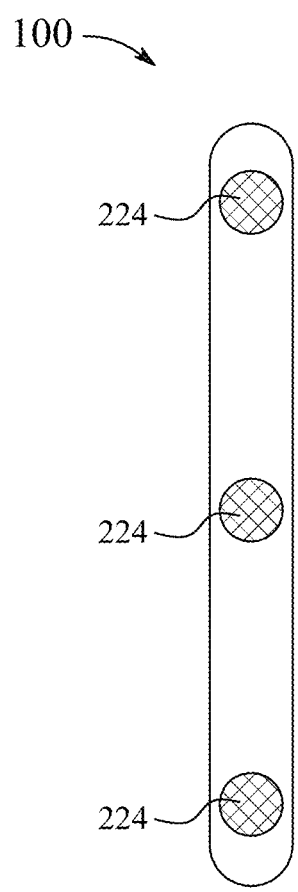
FIG. 2B is an exemplary illustration of a rear view of a brace strap of the smart knee brace system, according to certain embodiments.
Figure 2C:
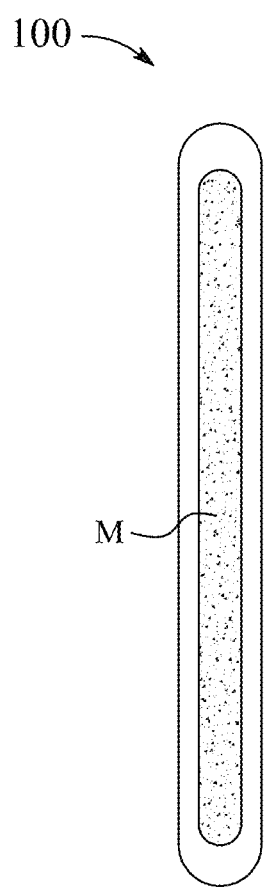
FIG. 2C is an exemplary illustration of a front view of the brace strap, according to certain embodiments.

FIG. 2B illustrates a rear view of the brace strap 108, according to an aspect of the present disclosure. Each brace strap 108 may include a fourth set of attachments 224 to removably attach to one or more of the knee brace 102, the thigh band 104, and the shin band 106. In a non-limiting example, each attachment 224 of the fourth set of attachments 224 may be a male part of a metal snap fastener configured to removably couple with the female part of corresponding metal snap fasteners on one or more of the knee brace 102, the thigh band 104, and the shin band 106. In an example, the brace strap 108 may include three attachments 224 as shown in FIG. 2B. Each attachment 224 of the fourth set of attachments 224 is configured to removably couple with one attachment 204 of the first set of attachments 204 on the knee brace 102, one attachment 214 of the second set of attachments 214 on the thigh band 104, and one attachment 216 of the third set of attachments 216 on the shin band 106. As such, the brace strap 108 may be selectively coupled between the knee brace 102 and the thigh band 104, the knee brace 102 and the shin band 106, or the thigh band 104 and the shin band 106. FIG. 2C illustrates an exemplary front view of the brace strap 108. In some aspects, the brace strap 108 may include a metal reinforcement strip "M" extending along a length thereof. In non-limiting examples, the brace strap 108 may be made from a hard leather or plastic.

Figure 2D:
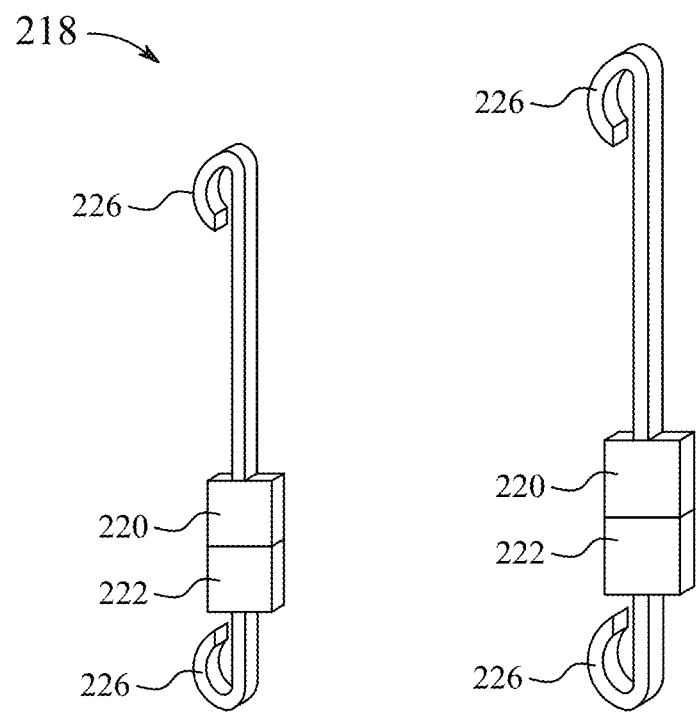
FIG. 2D is an exemplary illustration of an unexpanded configuration (left side) and an expanded configuration (right side) of a motion actuator of the smart knee brace system, according to certain embodiments.
Figure 2E:
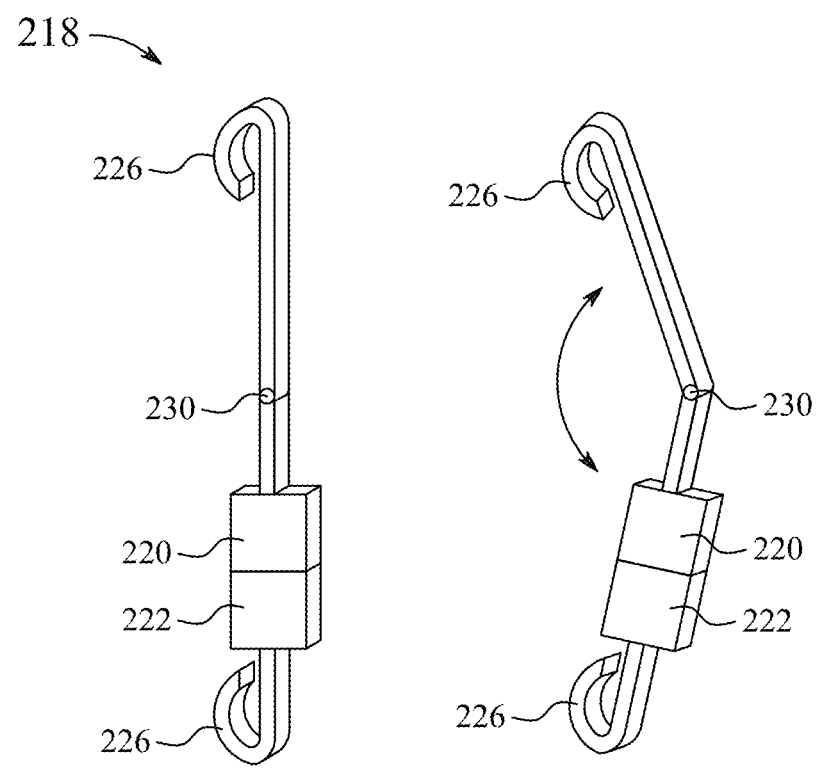
FIG. 2E is an exemplary illustration of a straight configuration (left side) and a bent configuration (right side) of the motion actuator of the smart knee brace system, according to certain embodiments.

FIG. 2D illustrates exemplary views of the motion actuators 218. Specifically, FIG. 2D illustrates a normal condition (left) and an expanded condition (right) of the motion actuator 218. Each motion actuator 218 may include metal hooks 226 at the ends thereof. In an aspect, the motor 220 is coupled to the sensor 222 as illustrated in FIG. 2D. In an aspect, the metal hooks 226 are configured to couple with metal loops 228 (see FIG. 2A) provided at ends of the brace straps 108. Alternatively, the material of the brace straps 108 may define pockets (not shown) to receive the metal hooks 226. For example, pockets may be defined in a hard leather brace strap or slits may be defined in a plastic brace strap to hold the metal hooks 226 of the motion actuator 218. When the patient tries to move the leg "L", orientation of the motion actuators 218 may change with respect to the knee brace 102 and the motion actuators 218 may either expand or experience a compression force. The sensors 222 are configured to sense the change in orientation and generate a signal, which is herein referred to as "the motion signal". FIG. 2E illustrates the normal condition (left) and a bent condition (right) of the motion actuator 218. In an aspect, the motion actuator 218 may include a hinge 230 that allows bending of the knee.

Referring back to FIG. 1, the system 100 further includes a computing device 110 having: (a) a circuitry including a communications device 112 and program instructions stored therein; and (b) a memory 114. In one aspect, the computing device 110 may include one or more processors operably coupled to the communications device 112. The computing device 110 may be embedded (shown through double-headed arrow) within the knee brace 102. In one aspect, the computing device 110 is communicably coupled to each of the motor 220 and the sensors 222. In one aspect, the communication between the computing device 110, the motor 220, and the sensor 222 may be established through the attachments of the brace straps 108 and the knee brace 102. The program instructions, when executed by the one or more processors, cause the one or more processors to receive the motion signals from the plurality of sensors 222 and measure a current range of motion of the thigh, the shin, and the knee, based on the received motion signals. Upon generation of the motion signal by the sensors 222, the computing device 110 may be configured to fetch the motion signals. In an aspect, a value of the received motion signal may be indicative of a type of movement of the leg "L". For example, a range of values for each type of motion of each of the thigh, the shin, and the knee may be stored in the memory 114 of the computing device 110. Based on the sensor 222 from which the motion signal is received and the value of the motion signals falling within a particular range of values stored therein, the computing device 110 may be configured to determine the type of motion and range of motion of each of the thigh, the shin, and the knee. The one or more processors of the computing device 110 is further configured to generate drive signals based on the measured current range of motion and transmit the drive signals to each of the plurality of motion actuators 218. As used herein, the term "drive signals" may refer to inputs generated by the computing device 110 to actuate the motor 220 of a desired motion actuator 218 to cause a forced movement of a respective portion of the leg "L". The drive signals may either induce a movement to the leg "L" to aid physical therapy or restrict a movement of the leg "L" to aid immobilization. In an aspect, the memory 114 may be configured to store a current set of physical therapy instructions and the drive signals may be configured to operate each motion actuator 218, such as the bi-directional linear actuator, to one of extend or retract in accordance with the current set of physical therapy instructions.

Figure 3A:
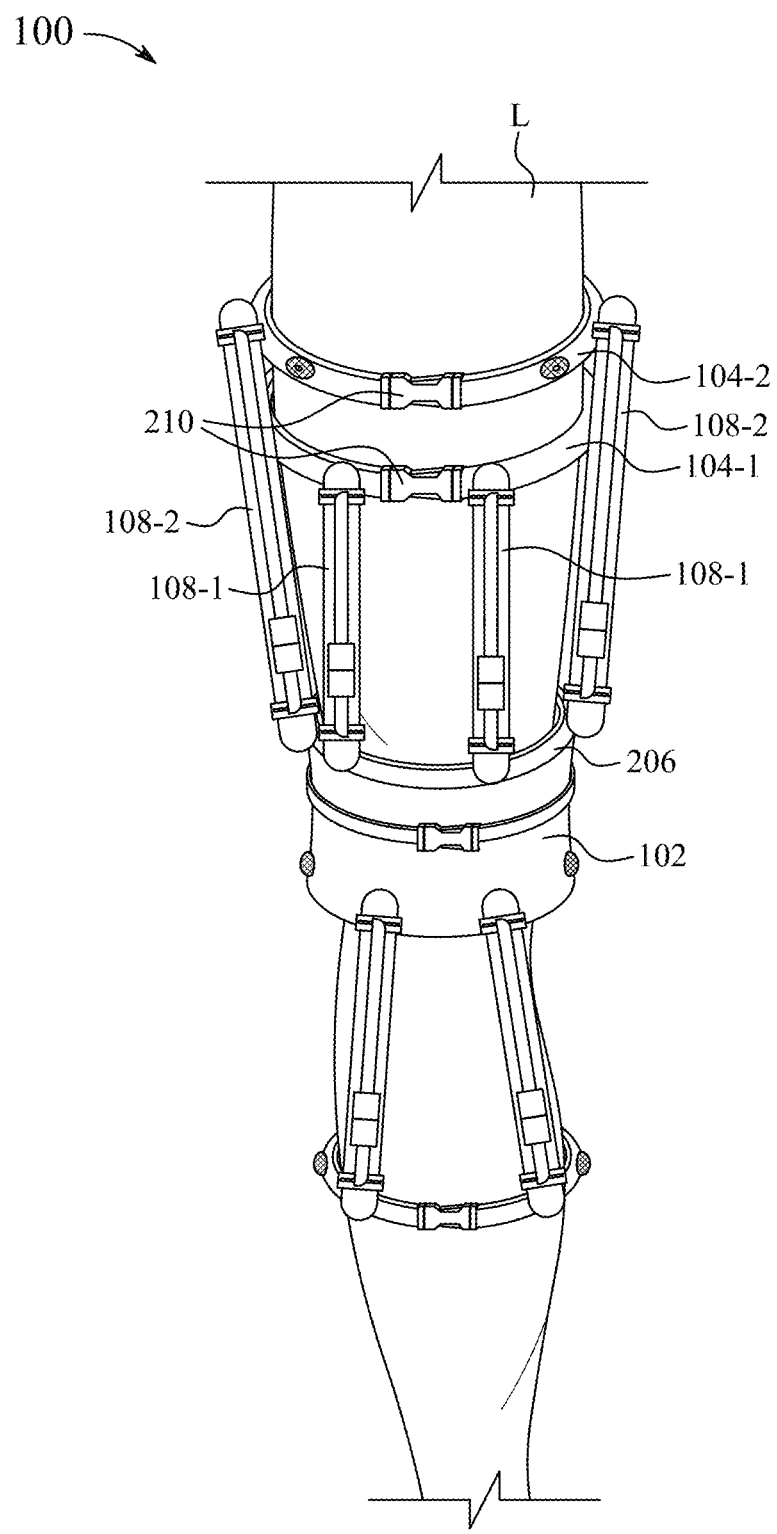
FIG. 3A is an exemplary illustration of smart knee brace system having multiple thigh bands, according to certain embodiments.
Figure 3B:
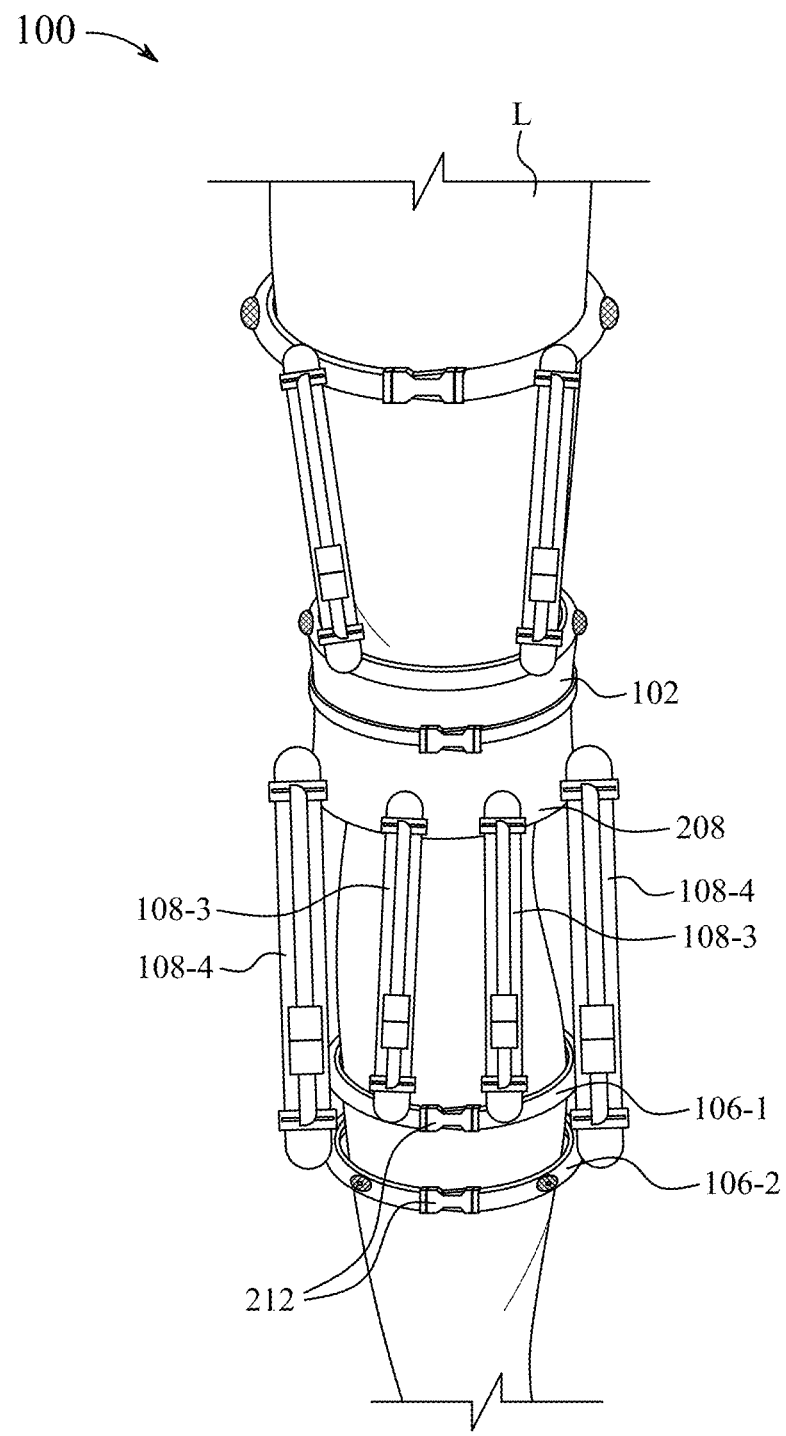
FIG. 3B is an exemplary illustration of smart knee brace system having multiple shin bands, according to certain embodiments.

FIG. 3A illustrates the system 100 having multiple thigh bands 104 installed on the thigh of the patient. In such an arrangement, multiple brace straps 108 may be attached between the thigh bands 104 and the knee brace 102. For example, a first pair of brace straps 108-1 may be attached to a first thigh band 104-1 and the first end 206 of the knee brace 102, and a second pair of brace straps 108-2 may be coupled to a second thigh band 104-2 and the first end 206 of the knee brace 102. Owing to a presence of the second strap 210, the thigh bands 104 may be secured at desired portion on the thigh. FIG. 3B illustrates the system 100 having multiple shin bands 106 installed on the shin of the patient. In such an arrangement, multiple brace straps 108 may be attached between the shin bands 106 and the knee brace 102. For example, a third pair of brace straps 108-3 may be coupled to a first shin band 106-1 and the second end 208 of the knee brace 102, and a fourth pair of brace straps 108-4 may be coupled to a second shin band 106-2 and the second end 208 of the knee brace 102. Owing to a presence of the third strap 212, the shin bands 106 may be secured at desired portion on the shin. FIG. 3A and FIG. 3B illustrates two thigh bands 104 and two shin bands 106 for the purpose of brevity. However, two or more thigh bands 104 and the shin bands 106 may be provided in the system 100. In one aspect, the arrangement illustrated in FIG. 3A may be combined with the arrangement illustrated in FIG. 3B.

Figure 3C:
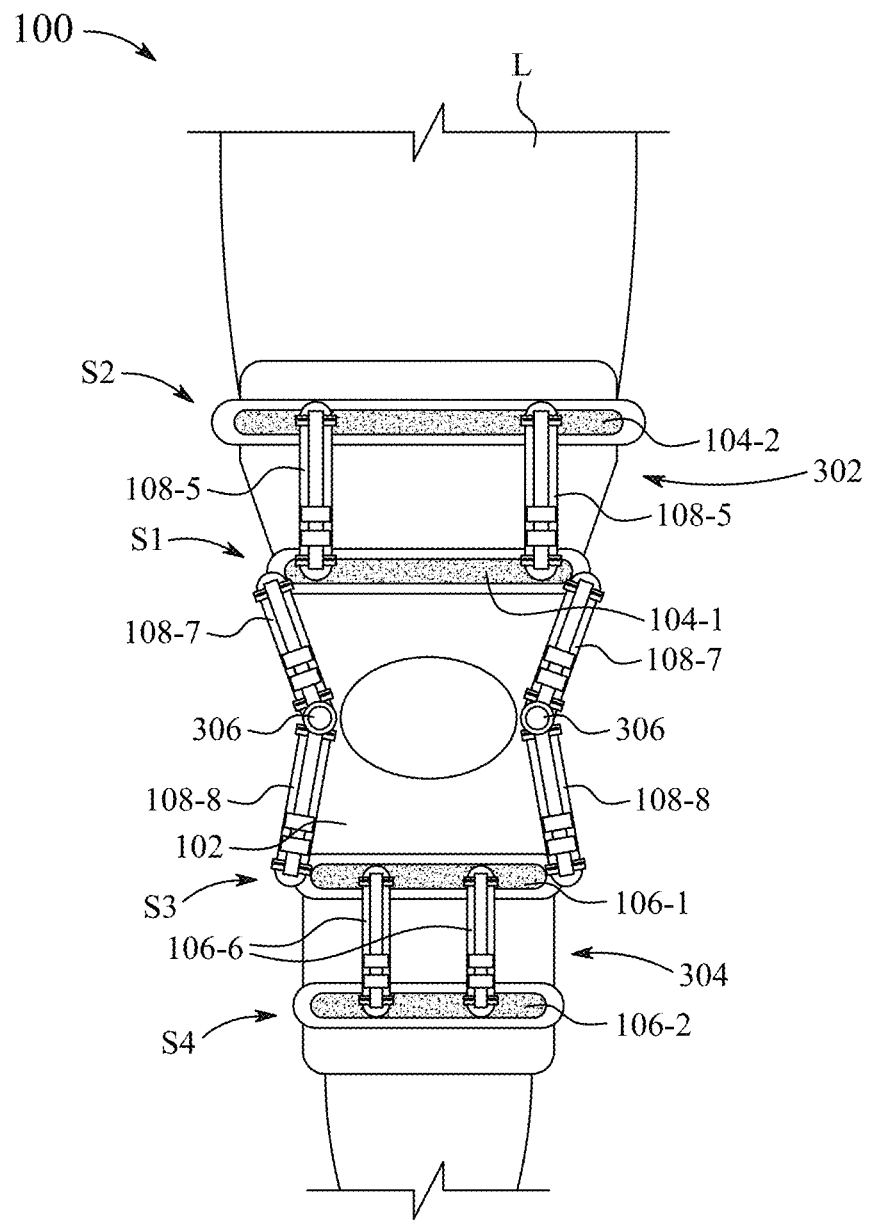
FIG. 3C is an exemplary illustration of smart knee brace system having multiple thigh bands, shin bands, and brace straps, according to certain embodiments.

FIG. 3C illustrates the system 100 having the brace straps 108 connecting the thigh band 104 and the shin band 106. According to an aspect, the system 100 includes an immobilization configuration that restricts movement of the leg "L" of the patient. The immobilization configuration includes the knee brace 102, one or more thigh bands 104, one or more shin bands 106, and one or more brace straps 108. In the immobilization configuration, the knee brace 102, in addition to surrounding the knee, may extend around some portion of the thigh and the shin. For example, the knee brace 102 surrounds the knee, a first portion 302 of the thigh and a second portion 304 of the shin. As used herein, the term "first portion" refers to a region proximal and above the knee, and the term "second portion" refers to a region proximal and below the knee. Further, in the immobilization configuration, one or more thigh bands 104 surround the knee brace 102 around the first portion 302 of the thigh and one or more shin bands 106 surround the knee brace 102 around the second portion 304 of the shin. Additionally, the one or more brace straps 108 are attached between the one or more thigh bands 104 and the knee brace 102, the one or more shin bands 106 and the knee brace 102, and the one or more thigh bands 104 and the one or more shin bands 106. As shown in FIG. 3C, a fifth pair of brace straps 108-5 are attached to the first thigh band 104-1 and the second thigh band 104-2, and a sixth pair of brace straps 108-6 are attached to the first shin band 106-1 and the second shin band 106-2. Further, two pairs of brace straps, such as a seventh pair 108-7 and an eight pair 108-8, are attached to the first thigh band 104-1 and the first shin band 106-1. In an aspect, the seventh pair of brace straps 108-7 may be attached to the eight pair of brace straps 108-8 via connectors 306 provided on the knee brace 102. The connectors 306 may remain stationary and hence may restrict flexure around the knee. Therefore, the thigh, the knee, and the shin may be restricted in movement with respect to each other. Such condition may be referred to as an immobilized condition. However, the patient may have a desire to move the portion of the leg "L" and bend the knee. Upon sensing slight movement, the sensors 222 attached on each brace strap 108 are configured to generate the motion signals. The computing device 110 receives the motion signals and accordingly transmits the drive signals to each of the motion actuators 218 to restrict the movement of the leg "L".

In FIG. 3C, each brace strap 108 includes the metal reinforcement strip extending along a respective length thereof. In such an arrangement, points of attachment for the brace straps 108 may be provided on the metal reinforcement strip. Also, the number of thigh bands 104, the shin bands 106, and the brace straps 108 shown in FIG. 3C are for mere illustration purpose and should not be construed limiting.

Figure 3D:
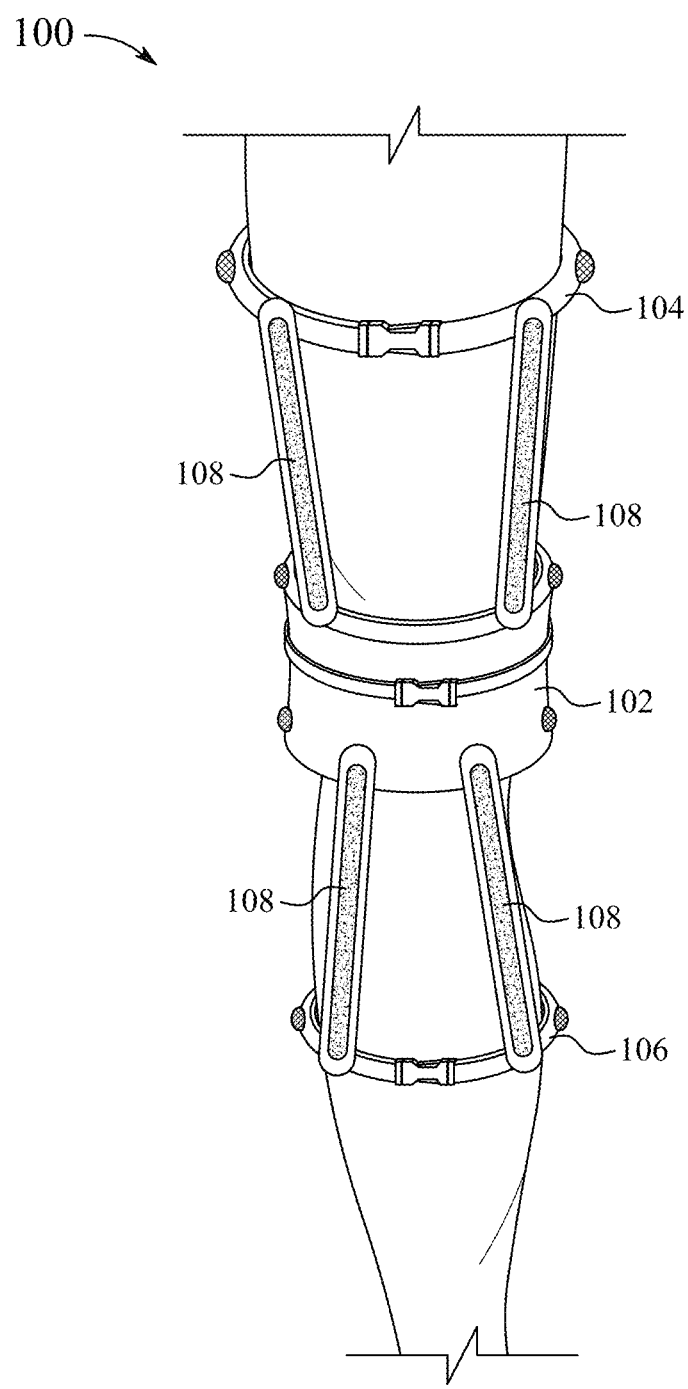
FIG. 3D is an exemplary illustration of smart knee brace system without the motion actuators, according to certain embodiments.
Figure 3E:
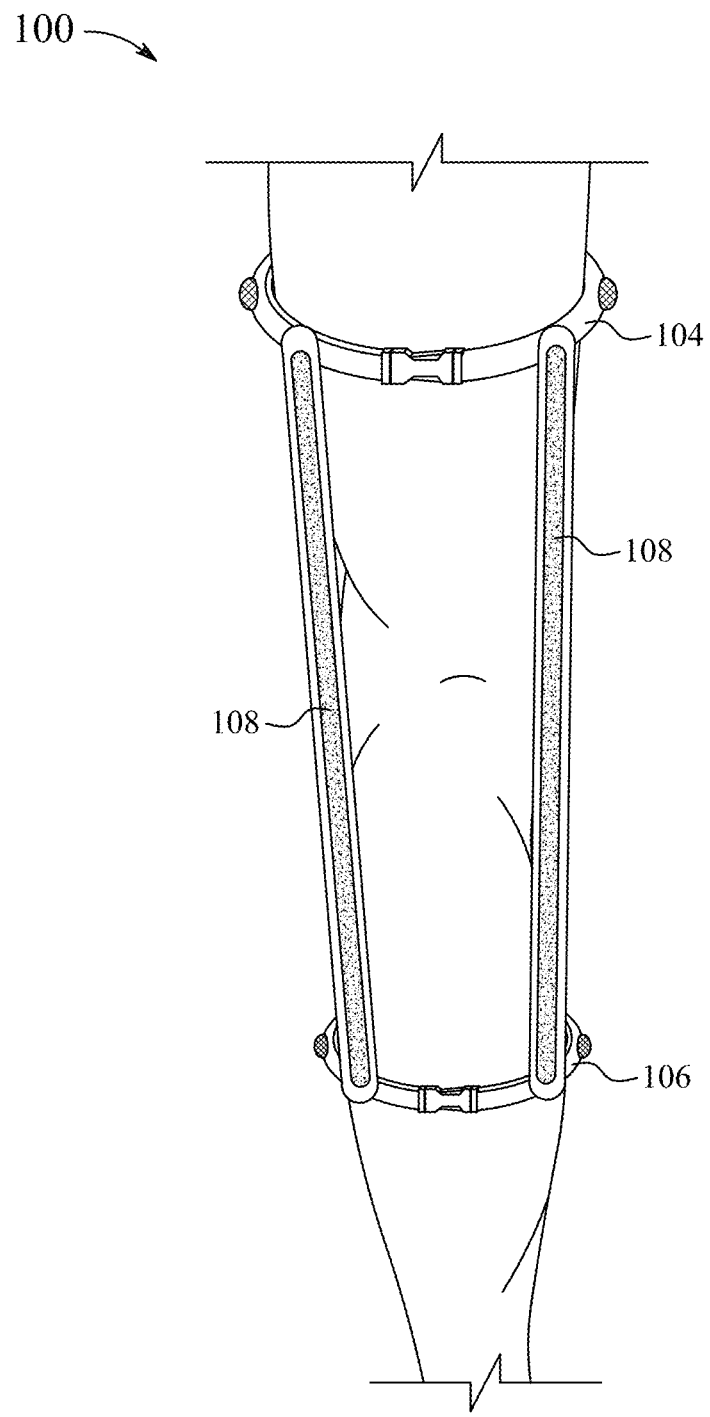
FIG. 3E is an exemplary illustration of smart knee brace system showing brace straps attached to the thigh band and the shin band, according to certain embodiments.

FIG. 3D illustrates the system 100 including actuator-less brace straps 108 for immobilization of the knee during initial healing after surgery. In an aspect, the motion actuators 218 may not be attached to the brace straps 108. In such an arrangement, the hard leather brace straps or the plastic brace straps may be used to connect the thigh band 104 to the knee brace 102 and the shin band 106 to the knee brace 102. In some aspects, the metal reinforcement strip may be provided on the hard leather brace straps, or the plastic brace straps, to add rigidity to the brace straps 108. In some aspects, the hard leather brace straps or the plastic brace straps, with or without the metal reinforcement strip, may be attached to the thigh band 104 and the shin band 106, without the knee brace 102 in between, as shown in FIG. 3E. With the thigh band 104 and shin band 106 secured to desired regions on the thigh and the shin respectively, such brace straps (as seen in FIG. 3E) may restrict bending of the knee and may, therefore, immobilize the leg "L".

According to another aspect of the present disclosure, the system 100 includes a physical therapy configuration. The physical therapy configuration includes the knee brace 102, the one or more thigh bands 104, the one or more shin bands 106, and the one or more brace straps 108. In the physical therapy configuration, the knee brace 102, in addition to surrounding the knee, surrounds the first portion 302 of the thigh and the second portion 304 of the shin. The physical therapy configuration is described with reference to FIG. 3A, FIG. 3B and FIG. 3C. In an aspect, the connectors 306 (as shown in FIG. 3C) may be movably coupled to the seventh pair of brace straps 108-7 and the eight pair of brace straps 108-8. Further, referring to FIG. 3C, a first subset "S1" of the one or more thigh bands 104 surrounds the knee brace 102 around the first portion 302 of the thigh; a second subset "S2" of the one or more thigh bands 104 surrounds the thigh above the first portion 302; a third subset "S3" of the one or more shin bands 106 surrounds the knee brace 102 around the second portion 304; and a fourth subset "S4" of the one or more shin bands 104 surrounds the shin below the second portion 304.

The one or more brace straps 108 are attached between at least one of the first subset "S1" and the knee brace 102, the second subset "S2" and the knee brace 102, the first subset "S1" and the second subset "S2", the third subset "S3" and the knee brace 102, the fourth subset "S4" and the knee brace 102, and the third subset "S3" and the fourth subset "S4". As seen in FIG. 3C, the seventh pair of brace straps 108-7 are attached to the first subset "S1" of the thigh bands 104 and the knee brace 102; the fifth pair of brace straps 108-5 are attached to the first subset "S1" and the second subset "S2" of the thigh bands 104; the eight pair of brace straps 108-8 are attached between the third subset "S3" of shin bands 106 and the knee brace 102; and the sixth pair of brace straps 108-6 are attached to the third subset "S3" and the fourth subset "S4". Herein, for the purpose of brevity, the each of the first subset "S1", the second subset "S2", the third subset "S3", and the fourth subset "S4" include one band. However, in some aspects, each subset may include two or more bands. Similar to the arrangement illustrated in FIG. 3A, the second pair of brace straps 108-2 may be attached to the second subset "S2" of thigh bands 104 and the knee brace 102; and similar to the arrangement illustrated in FIG. 3B, the fourth pair of brace straps 108-4 may be attached to the fourth subset "S4" of shin bands 106 and the knee brace 102. With such arrangement in the physical therapy configuration, the drive signals are configured to at least one of extend and retract the motion actuators 218 in accordance with the current set of physical therapy instructions. In one aspect, the current set of physical therapy instructions may include movements which need to be performed by the leg "L", scheduled for a predefined number of weeks. For example, phase-1 of the current set of physical therapy instructions may be scheduled for 0-2 weeks and may include leg raises for small height from the floor, holding the leg "L" in the raised position for few seconds, and the like. Similarly, other phases of the current set of physical therapy instructions may be scheduled for a period spanning for about 6 weeks.

In one aspect, the computing device 110 is configured to determine an amount of scar tissue in a knee joint based on the current range of motion. In one aspect, the computing device 110 is configured to sense an activity of the patient which indicates a desire to flex and/or straighten a knee joint based on a difference between the current range of motion and an expected range of motion. In cases where the motion signals from the sensors 222 located proximal to various regions of the thigh and the shin are associated with high value, the computing device 110 may determine such motion signals as the activity indicative of the desire to flex and/or straighten the knee joint. In an aspect, the expected range of motion may be set by a doctor or surgeon treating the patient. The current range of motion and the expected range of motion may be fed into the memory 114 of the computing device 110. Further, each of the current range of motion and the expected range of motion may be associated with a range of values of the motion signals. When a difference between a value of the received motion signals is beyond a predetermined threshold value, the computing device 110 may determine the activity as an indication of the desire to flex and/or straighten the knee joint by the patient.

Figure 4:
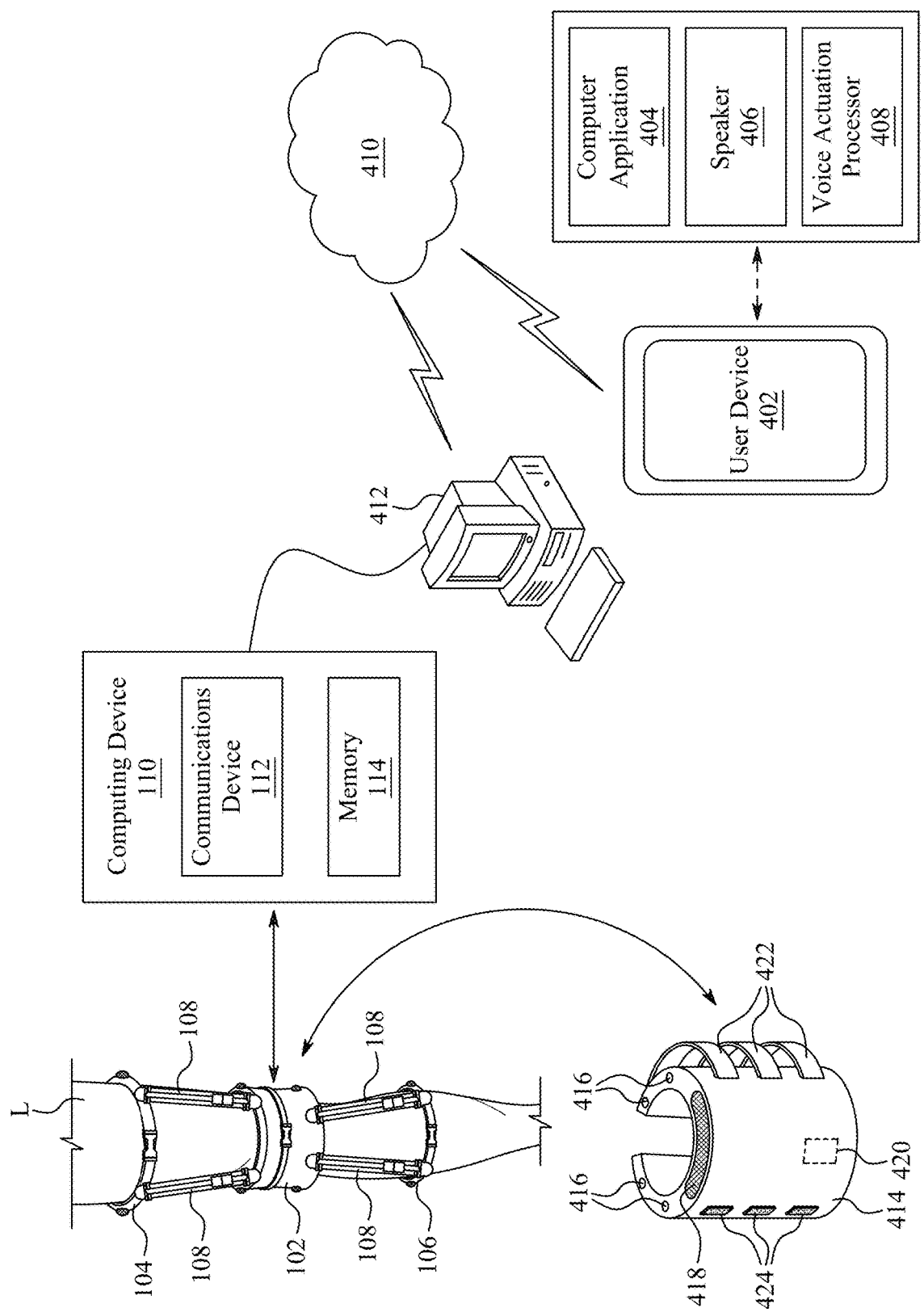
FIG. 4 is an exemplary network implementing the smart knee brace system, according to certain embodiments.

FIG. 4 illustrates a network diagram showing the system 100 being remotely connected to a user device 402. In a non-limiting example, the user device 402 may be a smartphone configured with a downloadable native smart brace computer application. In an aspect, the user device 402 is configured with a computer application 404, for example an android application or iOS application. The user device 402 also includes a speaker 406. The system 100 further includes a voice actuation processor 408 configured to generate voice signals. In one aspect, the voice actuation processor 408 may be provided in the user device 402 and may be operably coupled to the speaker 406, where the voice signals are applied to the speaker 406 to generate voice commands.

According to an aspect, the native smart brace computer application 404 is in bidirectional communication with the computing device 110, via an application server 410. Connection between the computing device 110 and the native smart brace computer application 404 in the user device 402 may be established via a wireless network (described later with respect to FIG. 5). In some aspects, the computing device 110 may be connected to a diagnosis system 412 and the diagnosis system 412 may be connected to the native smart brace computer application 404 via the application server 410. In one aspect, the diagnosis system 412 may be located in a therapy room. The application server 410 may be dedicated to host services and functions that may be executed by the computer application 404. Additionally, the application server 410 may store information regarding the patient, prescribed physical therapy instructions, and other details, such as data related to injury caused to the leg "L". With the capability of such storage in the application server 410, the native smart brace computer application 404 may fetch required data from the application server 410 relating to the patient. In one aspect, the user device 402 may be accessed by one of the patient, a caregiver, a physical therapist, and an orthopedic doctor.

The native smart brace computer application 404 is configured to receive the current range of motion from the communications device 112, compare the current range of motion to the expected range of motion, and determine an effectiveness of the current set of physical therapy instructions based on the comparison. The determined effectiveness may be indicative of healing of the injury caused to the leg "L" and a progress shown by the patient with respect to the current set of physical therapy instructions. The native smart brace computer application 404 may be configured to determine the effectiveness as a value and on a display the value on a screen of the user device 402. When the effectiveness is beyond a predefined threshold, the native smart brace computer application 404 is configured to generate a set of modified physical therapy instructions based on the determined effectiveness. Further, a modified physical therapy schedule is generated based on the set of modified physical therapy instructions. The native smart brace computer application 404 may be configured to modify a previously prescribed schedule with respect to the current set of physical therapy instructions, to generate the modified physical therapy instructions. For example, the 0-2 weeks schedule for the phase-1 exercise may be changed to 1-week, or additional phases of exercises to be performed may be added to the modified physical therapy instructions, based on the determined effectiveness.

The native smart brace computer application 404 is further configured to transmit data related to the modified physical therapy schedule to the communications device 112 and notify one or more of the patient, the caregiver, the physical therapist, and the orthopedic doctor. For example, the modified physical therapy schedule may be edited by the orthopedic doctor via the computer application 404 and the data related to the modified physical therapy schedule may be transmitted to the communications device 112. In another example, the modified physical therapy schedule may be transmitted to the diagnosis system 412, so that the caregiver and the physical therapist are aware of the exercises. Upon receiving the modified physical therapy schedule by the communications device 112, the computing device 110 may be configured to generate drive signals, based on the schedule, and actuate the motion actuators 218 to implement the modified physical therapy instructions. In one aspect, multiple user devices, with each having the native smart brace computer application 404 installed therein, may be communicably coupled to the communications device 112. However, the patient, the caregiver, or the orthopedic doctor may restrict access to few parameters and actions to be taken in few of such user devices. The voice actuation processor 408 is configured to generate the voice signals based on the modified physical therapy schedule. The voice signals are applied to the speaker 406 to generate voice commands to inform the patient of a contract time and a relax time. The terms "contract time" and the "relax time" used herein should not be construed as limitation. The voice signals may guide the patient to follow the modified physical therapy instructions. In a non-limiting example, the voice signals applied to the speaker 406 may inform the patient to raise the leg to 30 degree angle, hold the leg for 5 seconds, slowly bring back the leg to rest position, and the like. In one aspect, the voice commands may instruct the patient to one of: add compression to the knee brace 102 by wrapping a sleeve 414 tightly or loosely around the knee brace 102; add compression to the thigh band 104 by wrapping the sleeve 414 tightly or loosely around the thigh band 104; or add compression to the shin band 106 by wrapping the sleeve 414 tightly or loosely around the shin band 106.

In an aspect, the system 100 further includes the sleeve 414 configured to surround one of the knee brace 102, the thigh band 104, and the shin band 106. In one aspect, the sleeve 414 may include multiple straps 422 configured to surround the knee joint and attach with a securing portion 424 to secure the sleeve 414 on the knee brace 102. The system 100 further includes an electronically controlled cooling coil 416 and an electronically controlled heating element 418, both located within the sleeve 414. Since the sleeve 414 is electrically controlled, requirement of ice and water to regulate the temperature of the sleeve 414 may be eliminated. Additionally, at least one temperature sensor 420 is located within the sleeve 414 and communicably coupled to the computing device 110. The temperature sensor 420 is configured to generate temperature signals. The temperature sensor 420 may consist of at least one thermocouple, RTD (resistance temperature detector), thermistor and a semiconductor based integrated circuit.

In one aspect, the current set of physical therapy instructions includes temperature control instructions in addition to the exercises to be performed by the patient, as described earlier. In one aspect, the sleeve 414 may include a temperature modulation subsystem that is configured to provide a surface that abuts the skin of the patient in a region where the patient desires hot and/or cold therapy.

The computing device 110 is configured to receive the temperature signals from the temperature sensor 420, fetch the temperature control instructions from the memory 114, analyze the temperature signals, and transmit the temperature control signals to one of the electronically controlled cooling coil 416 or the electronically controlled heating element 418 in accordance with the temperature control instructions.

To this end, the system 100 of present disclosure emphasizes an ability to convert the brace straps 108 from a rigid configuration to a continuous passive motion (CPM) configuration, for example, by: (a) providing drive signals to aid flexion/extension exercises, and (b) allowing to selectively detach the brace straps 108. For patients, specifically older patients, the system 100 can assist in forcing the knee both actively and passively to stretch the quad, strengthen the hamstring and mobilize the knee joint. The system 100 also aids immobilization as instructed by doctors to limit range of motion of the knee, and stabilization through physical therapy as instructed by the doctors. Since the system 100 is communicably coupled to the computer application 404, therapists and surgeons may create, add, or edit the physical therapy prescribed to the patient and also track progress remotely. For example, the native smart brace computer application 404 may be downloaded on devices at hospitals to track progress of the patient with respect to the prescribed physical therapy. Similarly, the patient may also be able to download the native smart brace computer application 404 and track the progress.

Figure 5:
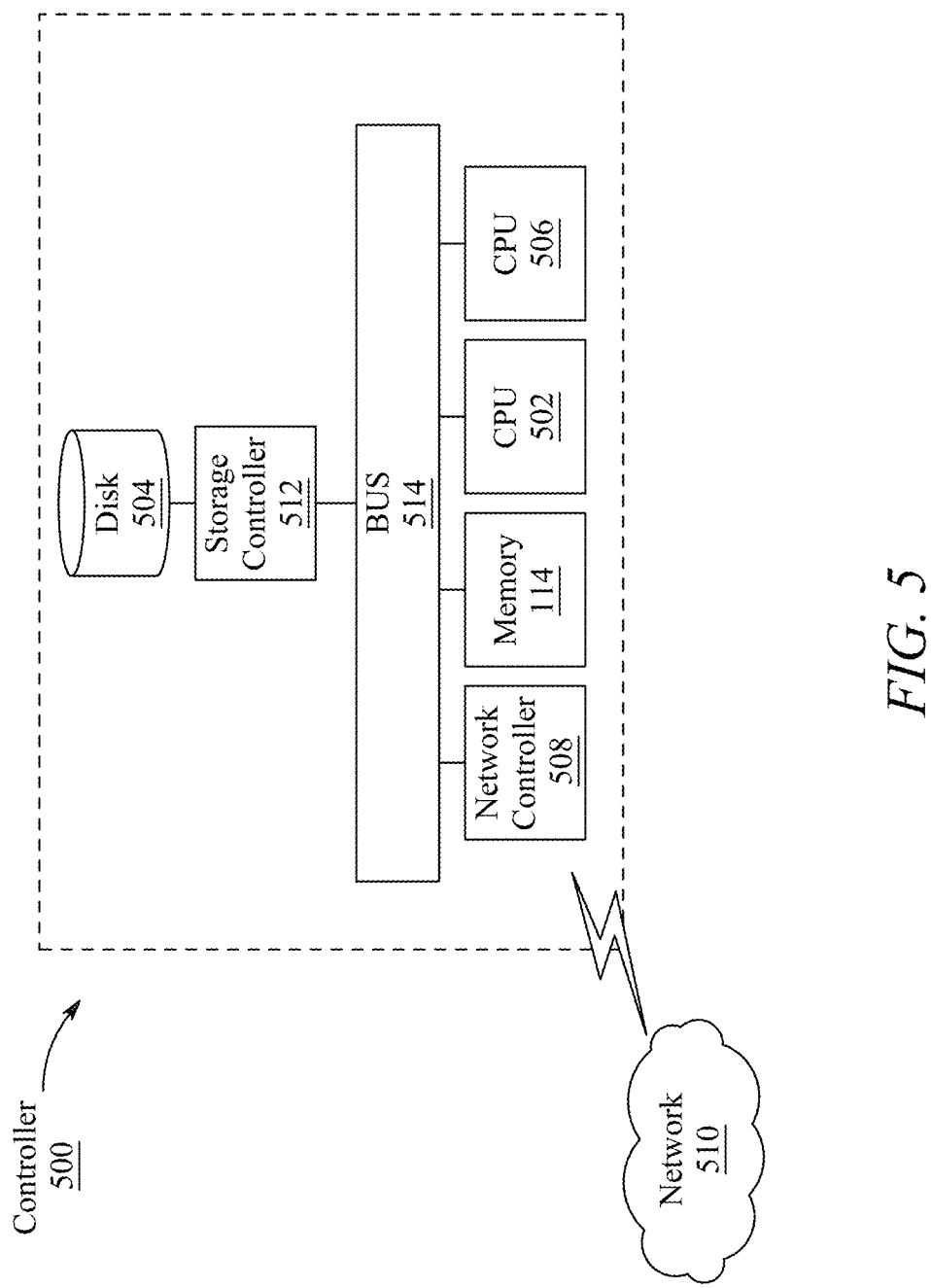
FIG. 5 is an illustration of a non-limiting example of details of a computing hardware used in the smart knee brace system, according to certain embodiments.

Next, details of the hardware description of the computing device 110 of FIG. 1 according to exemplary embodiments are described with reference to FIG. 5. In FIG. 5, a controller 500 is described as a representative of the computing device 110 which includes a CPU 502 which performs the processes described above/below. The process data and instructions may be stored in the memory 114 (also shown in FIG. 1). These processes and instructions may also be stored on a storage medium disk 504, such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, FPGAS, ASICS, or any hard disk or any other information processing device with which the controller 500 communicates, such as a server or computer.

Further, the claims may be provided as a utility application, background daemon, or component of an operating system, or combination thereof, executing in conjunction with CPU 502, 506 and an operating system such as Microsoft Windows 7, Microsoft Windows 10, UNIX, Solaris, LINUX, Apple MAC-OS, and other systems known to those skilled in the art.

The hardware elements in order to achieve the controller 500 may be realized by various circuitry elements, known to those skilled in the art. For example, the CPU 502 or the CPU 506 may be a Xenon or Core processor from Intel of America or an Opteron processor from AMD of America, or may be other processor types that would be recognized by one of ordinary skill in the art. Alternatively, the CPU 502, 506 may be implemented on an FPGA, an ASIC, a PLD or using discrete logic circuits, as one of an ordinary skill in the art would recognize. Further, the CPU 502, 506 may be implemented as multiple processors cooperatively working in parallel to perform the instructions of the inventive processes described above.

The controller 500 also includes a network controller 508, such as an Intel Ethernet PRO network interface card from Intel Corporation of America, for interfacing with a network 510. As can be appreciated, the network 510 can be a public network, such as the Internet, or a private network, such as an LAN or WAN network, or any combination thereof and can also include PSTN or ISDN sub-networks. The network 510 can also be wired, such as an Ethernet network, or can be wireless, such as a cellular network including EDGE, 3G, 4G and 5G wireless cellular systems. The wireless network can also be WiFi, Bluetooth, or any other wireless form of communication that is known.

A general purpose storage controller 512 connects the storage medium disk 504 with a communication bus 514, which may be an ISA, EISA, VESA, PCI, or similar, for interconnecting all of the components of the controller 500. A description of the general features and functionality of the storage controller 512 and the network controller 508 is omitted herein for brevity as these features are known.

The exemplary circuit elements described in the context of the present disclosure may be replaced with other elements and structured differently than the examples provided herein. Moreover, the circuitry configured to perform features described herein may be implemented in multiple circuit units (e.g., chips), or the features may be combined in the circuitry on a single chipset, as shown on FIG. 6.

Figure 6:
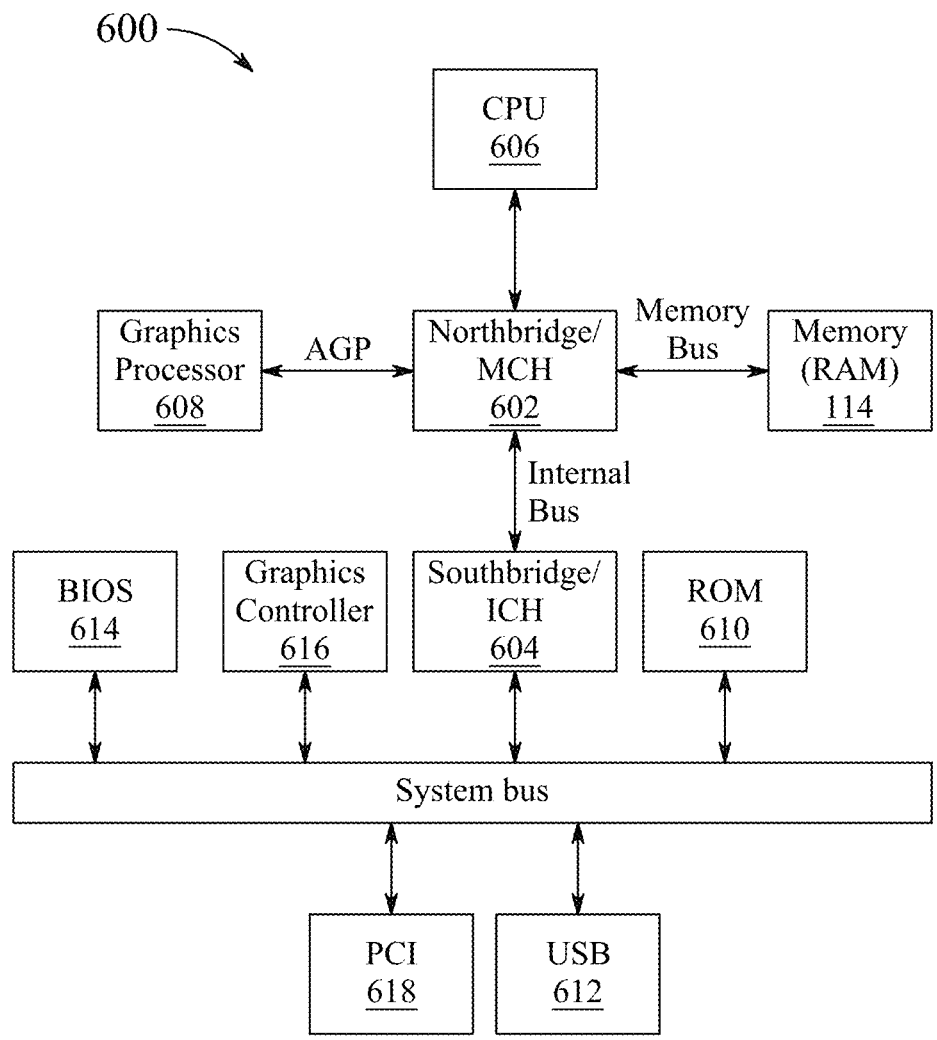
FIG. 6 is an exemplary schematic diagram of a data processing system used within the computing hardware, according to certain embodiments.

FIG. 6 shows a schematic diagram of a data processing system 600, according to certain embodiments, for performing the functions of the exemplary embodiments. The data processing system 600 is an example of a computer in which a code or instructions implementing the processes of the illustrative embodiments may be located.

In FIG. 6, the data processing system 600 employs a hub architecture including a north bridge and memory controller hub (NB/MCH) 602 and a south bridge and input/output (I/O) controller hub (SB/ICH) 604. A central processing unit (CPU) 606 is connected to NB/MCH 602. The NB/MCH 602 also connects to the memory 114 (shown in FIG. 1) via a memory bus and connects to a graphics processor 608 via an accelerated graphics port (AGP). The NB/MCH 602 also connects to the SB/ICH 604 via an internal bus (for example, a unified media interface or a direct media interface). The CPU 606 may contain one or more processors and even may be implemented using one or more heterogeneous processor systems.

Figure 7:
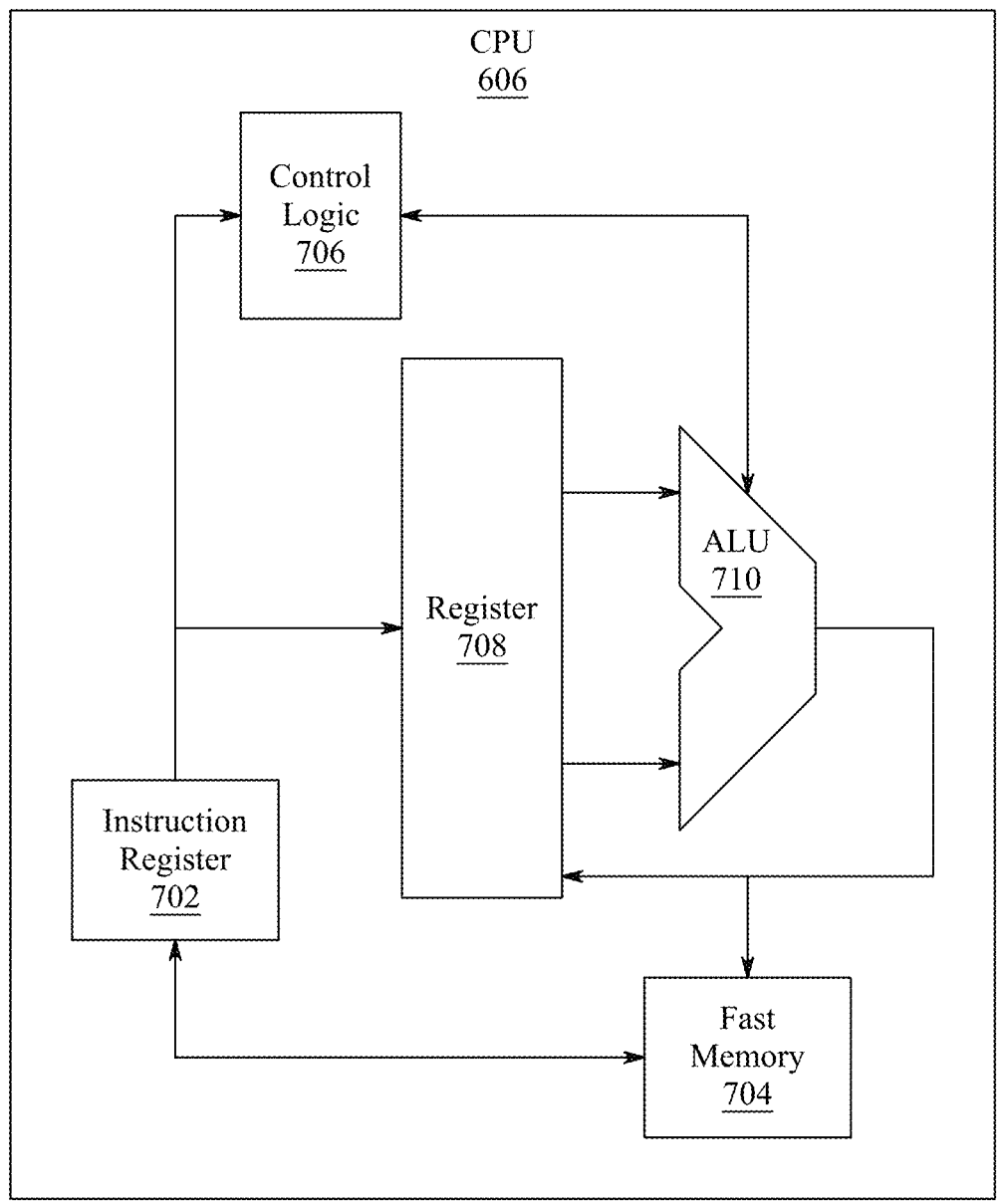
FIG. 7 is an exemplary schematic diagram of a processor used with the computing hardware, according to certain embodiments.

For example, FIG. 7 shows one implementation of the CPU 606. In one implementation, an instructions register 702 retrieves instructions from a fast memory 704. At least part of these instructions is fetched from the instructions register 702 by a control logic 706 and interpreted according to the instruction set architecture of the CPU 606. A part of the instructions can also be directed to a register 708. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using an arithmetic logic unit (ALU) 710 that loads values from the register 708 and performs logical and mathematical operations on the loaded values according to the instructions. The results from these operations can be feedback into the register and/or stored in the fast memory 704. According to certain implementations, the instruction set architecture of the CPU 606 can use a reduced instruction set architecture, a complex instruction set architecture, a vector processor architecture, a very large instruction word architecture. Furthermore, the CPU 830 can be based on the Von Neuman model or the Harvard model. The CPU 606 can be a digital signal processor, an FPGA, an ASIC, a PLA, a PLD, or a CPLD. Further, the CPU 606 can be an x86 processor by Intel or by AMD; an ARM processor, a Power architecture processor by, for example, IBM; a SPARC architecture processor by Sun Microsystems or by Oracle; or other known CPU architecture.

Referring again to FIG. 6, in the data processing system 600, the SB/ICH 604 is coupled through a system bus to a read only memory (ROM) 610, a universal serial bus (USB) port 612, a flash binary input/output system (BIOS) 614, and a graphics controller 616. PCI/PCIe devices can also be coupled to the SB/ICH 604 through a PCI bus 618. The PCI devices may include, for example, Ethernet adapters, add-in cards, and PC cards for notebook computers.

Figure 8:
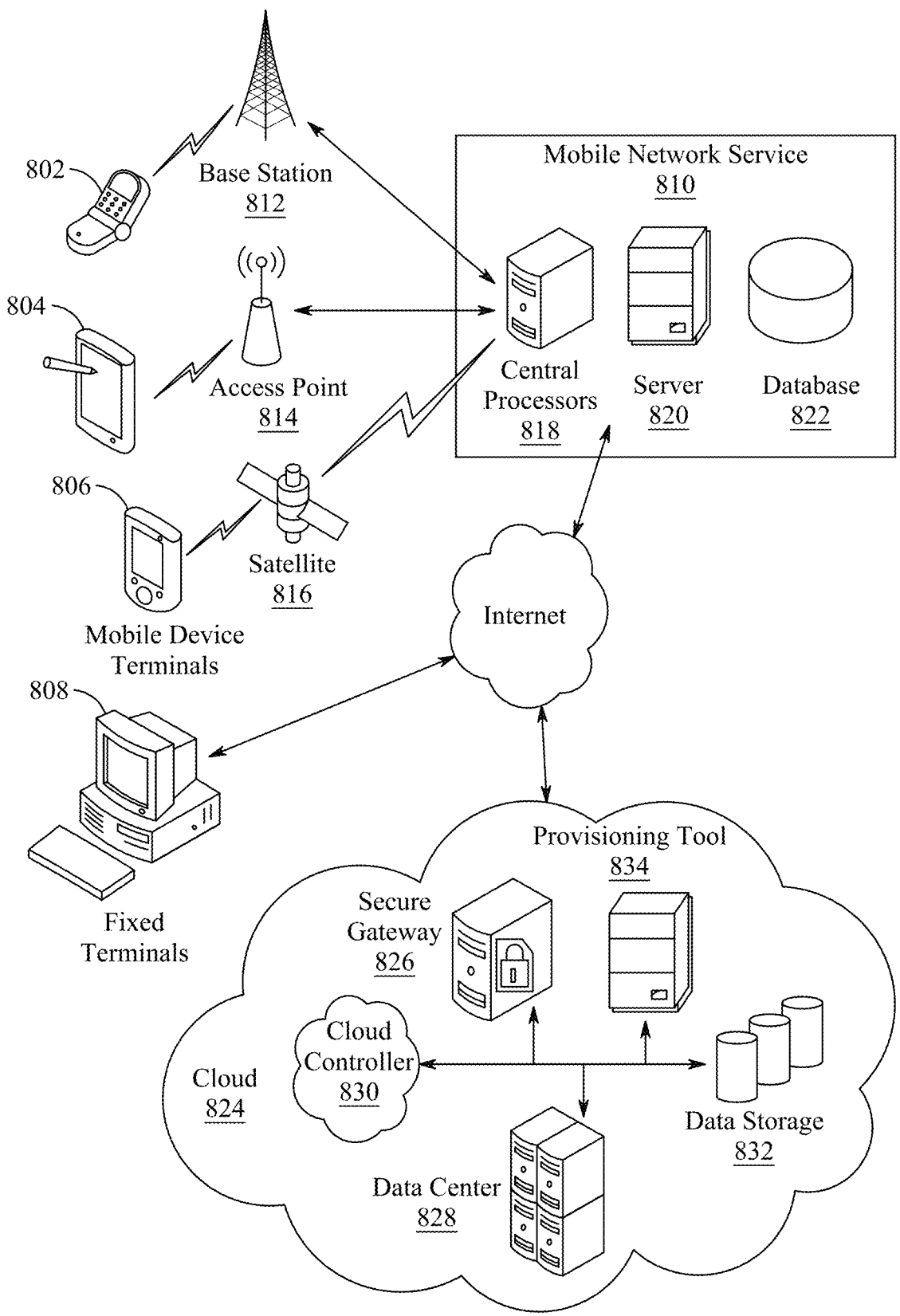
FIG. 8 is an illustration of a non-limiting example of distributed components which may share processing with the computing hardware, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 8, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Figure 9A:
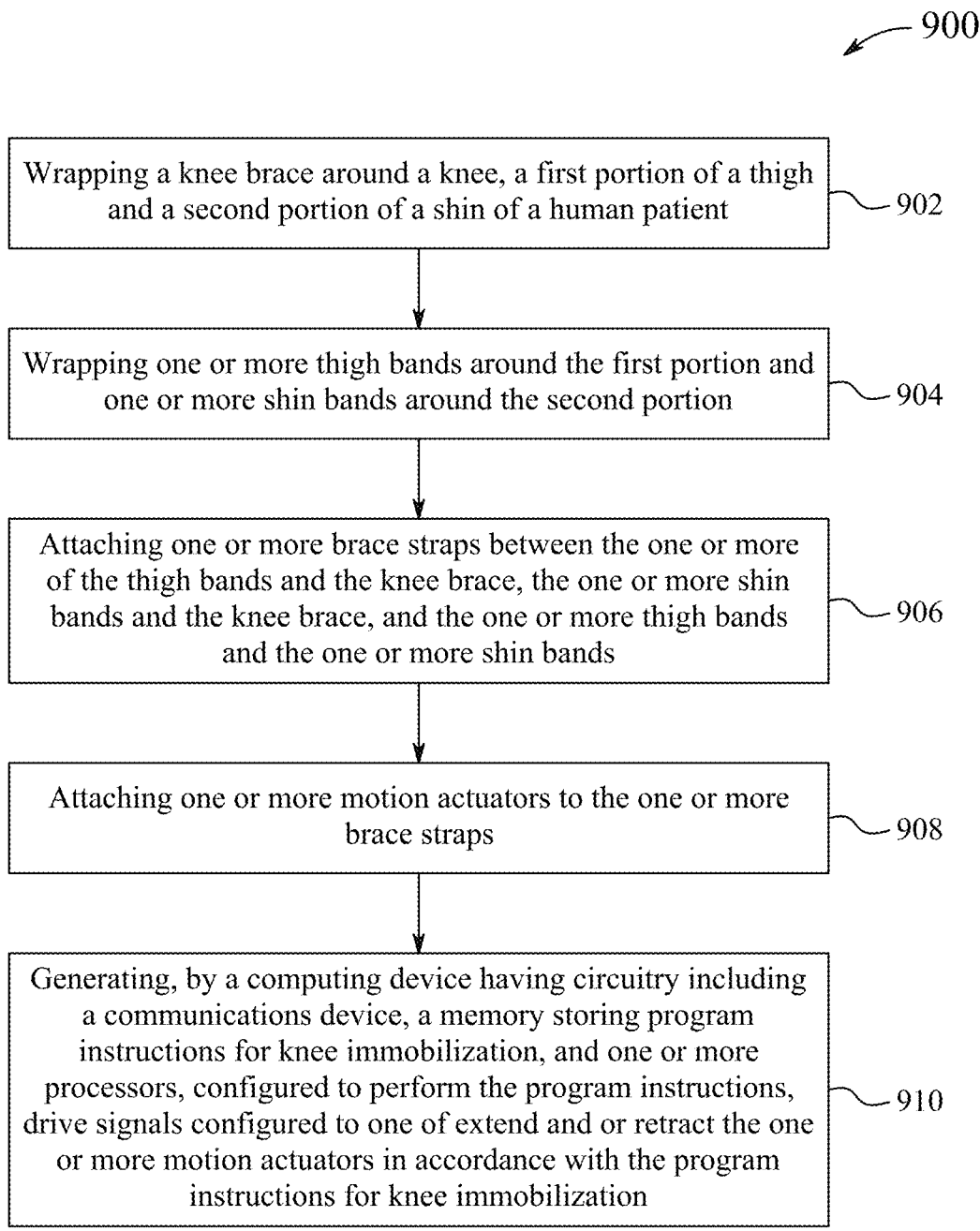
FIG. 9A is an exemplary flowchart of a method for immobilizing a knee with the smart knee brace system, according to certain embodiments.

FIG. 9A illustrates a flowchart of a method 900 for immobilizing the knee with the system 100. The method 900 will be described in conjunction with FIG. 1 to FIG. 4. At step 902, the method 900 includes wrapping the knee brace 102 around the knee, the first portion 302 of the thigh and the second portion 304 of the shin of the patient.

At step 904, the method 900 includes wrapping one or more thigh bands 104 around the first portion 302 and one or more shin bands 106 around the second portion 304.

At step 906, the method 900 includes attaching the one or more brace straps 108 between the one or more thigh bands 104 and the knee brace 102, the one or more shin bands 106 and the knee brace 102, and the one or more thigh bands 104 and the one or more shin bands 106.

At step 908, the method 900 includes attaching one or more motion actuators 218 to the one or more brace straps 108.

At step 910, the method 900 includes generating, by the computing device 110 having a circuitry including the communications device 112, the memory 114 storing program instructions for knee immobilization, and one or more processors, configured to perform the program instructions, drive signals configured to one of extend or retract the one or more motion actuators 218 in accordance with the program instructions for knee immobilization. In one aspect, the program instructions may be one of the current set of physical therapy instructions or the modified physical therapy instructions.

Although not explicitly illustrated in FIG. 9A, the method 900 further includes wrapping the sleeve 414 around the knee brace 102, where the sleeve 414 is configured with the electronically controlled cooling coil 416 and the electronically controlled heating element 418. The method 900 further includes measuring the temperature of the sleeve 414 with the temperature sensor 420. In an aspect, the temperature sensor 420 may be embedded within the sleeve 414. The method 900 further includes generating temperature signals and transmitting the temperature signals to the computing device 110. In one aspect, the computing device 110 may be communicably coupled with the temperature sensor 420 to receive the temperature signals. The method 900 includes performing one of: (a) applying a first electrical current to the electronically controlled cooling coil 416 until the temperature of the sleeve 414 is lowered to a first temperature in accordance with the program instructions for the knee immobilization; or (b) applying a second electrical current to the electronically controlled heating device 418 until the temperature of the sleeve 414 is raised to a second temperature in accordance with the program instructions for the knee immobilization. In one aspect, the application of the first electrical current and the second electrical current may be achieved with a help of a battery disposed within the sleeve 414.

The method 900 further includes performing, in accordance with the program instructions for the knee immobilization, one or more of: (a) compressing the knee brace 102 by wrapping the sleeve 414 tightly or loosely around the knee brace 102; (b) compressing the one or more thigh bands 104 by wrapping the sleeve 414 tightly or loosely around the one or more thigh bands 104; and (c) compressing the one or more shin bands 106 by wrapping the sleeve 414 tightly or loosely around the one or more shin bands 106.

Figure 9B:
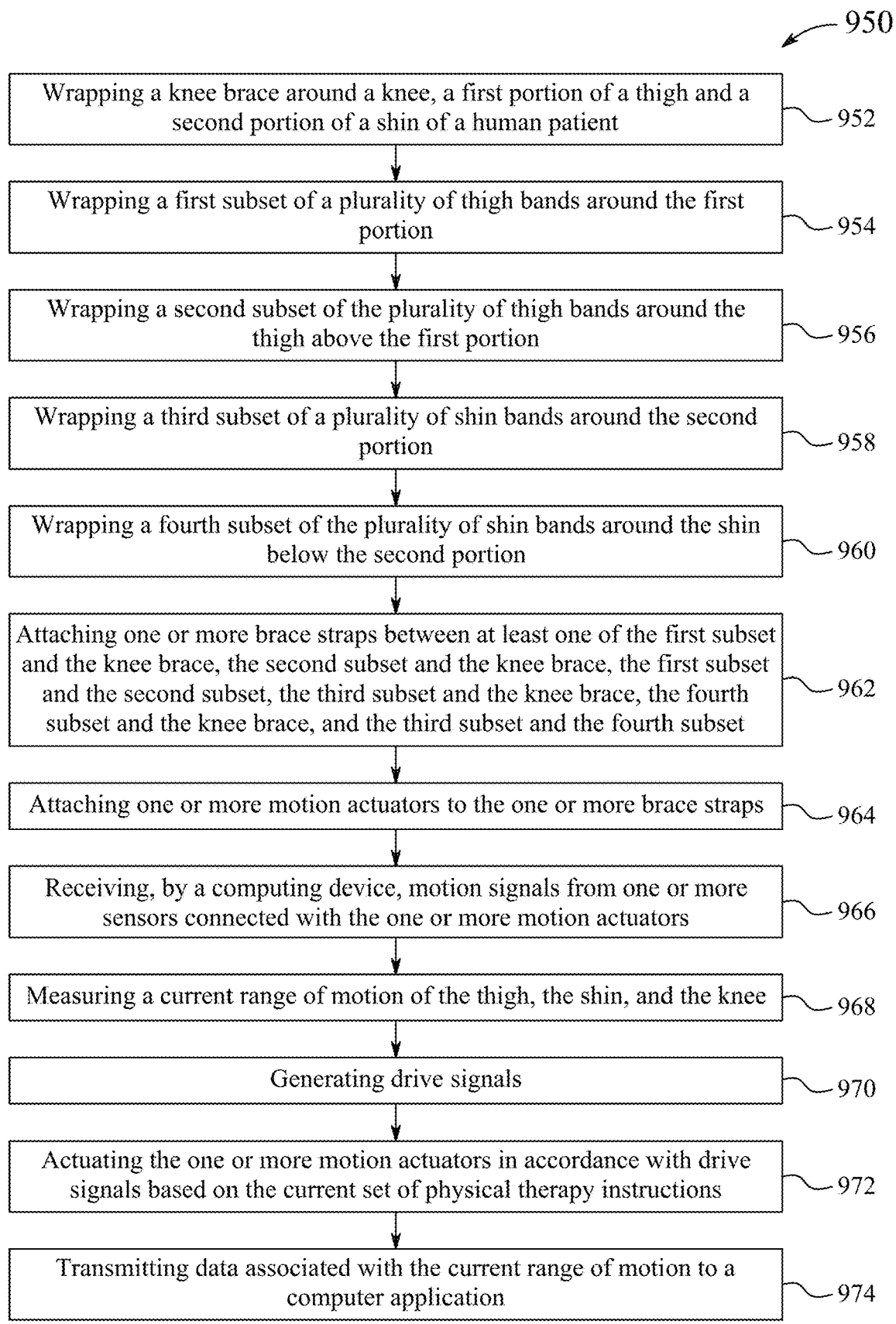
FIG. 9B is an exemplary flowchart of a method of performing physical therapy with the smart knee brace system, according to certain embodiments.

FIG. 9B illustrates a flowchart of a method 950 of performing physical therapy with the system 100. The method 950 will be described in conjunction with FIG. 1 to FIG. 4. At step 952, the method 950 includes wrapping the knee brace 102 around the knee, the first portion 302 of the thigh and the second portion 304 of the shin of the patient.

At step 954, the method 950 includes wrapping the first subset "S1" of the plurality of thigh bands 104 around the first portion 302.

At step 956, the method 950 includes wrapping the second subset "S2" of the plurality of thigh bands 104 around the thigh above the first portion 302.

At step 958, the method 950 includes wrapping the third subset "S3" of the plurality of shin bands 106 around the second portion 304.

At step 960, the method 950 includes wrapping the fourth subset "S4" of the plurality of shin bands 106 around the shin below the second portion 304.

At step 962, the method 950 includes attaching one or more brace straps 108 between at least one of the first subset "S1" and the knee brace 102, the second subset "S2" and the knee brace 102, the first subset "S1" and the second subset "S2", the third subset "S3" and the knee brace 102, the fourth subset "S4" and the knee brace 102, and the third subset "S3" and the fourth subset "S4".

At step 964, the method 950 includes attaching one or more motion actuators 218 to the one or more brace straps 108.

At step 966, the method 950 includes receiving, by the computing device 110 having a circuitry including the communications device 112, the memory 114 storing the current set of physical therapy instructions, and one or more processors configured to perform the current set of physical therapy instructions, the motion signals from one or more sensors 222 connected with the one or more motion actuators 218.

At step 968, the method 950 includes measuring the current range of motion of the thigh, the shin, and the knee.

At step 970, the method 950 includes generating the drive signals.

At step 972, the method 950 includes actuating the one or more motion actuators 218 in accordance with drive signals based on the current set of physical therapy instructions.

At step 974, the method 950 includes transmitting data associated with the current range of motion to the computer application 404.

Although not explicitly illustrated in FIG. 9B, the method 950 further includes accessing, by the computing device 110, the expected range of motion from the current set of physical therapy instructions; comparing, by the computing device 110, the current range of motion to the expected range of motion. When the current range of motion matches the expected range of motion, the method 950 includes generating, by the computing device 110, the drive signals. When the current range of motion is less than or greater than the expected range of motion, the method 950 includes generating, by the computing device 110, a report regarding an effectiveness of the physical therapy schedule including the current set of physical therapy instructions.

The method 950 further includes receiving, by the user device 402, the current range of motion from the communications device 112. The user device 402 is configured with the computer application 404 in a bidirectional communication with the computing device 110. The method 950 further includes comparing the current range of motion to the expected range of motion; determining the effectiveness of the current set of physical therapy instructions; generating a set of modified physical therapy instructions based on the determined effectiveness; generating a modified physical therapy schedule based on the set of modified physical therapy instructions; transmitting data related to the modified physical therapy schedule to the communications device 112; updating the current set of physical therapy instructions with the set of modified physical therapy instructions; and notifying one or more of the patient, the caregiver, the physical therapist, and the orthopedic doctor of the modified physical therapy schedule.

The method 950 further includes generating voice signals by the user device 402 based on one of the current physical therapy instructions and the set of modified physical therapy instructions; and applying the voice signals to the speaker 402 of the user device 402 to produce voice commands regarding the contract time and the relax time.

The method 950 further includes determining, by the computing device 110, an amount of scar tissue in the knee joint based on the current range of motion; calculating, by the computing device 110, a difference between the current range of motion and the expected range of motion; and identifying, by the computing device 110, motion which indicates a desire by the patient to flex and/or straighten the knee joint based on the difference between the current range of motion and the expected range of motion.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A smart knee brace system, comprising:
a knee brace configured to wrap around and support a knee of a human patient;
a plurality of thigh bands, each thigh band configured to wrap around a thigh of the human patient;
a plurality of shin bands, each shin band configured to wrap around a shin of the human patient;
a plurality of adjustable brace straps configured to removably attach to one or more of the knee brace, the thigh bands, and the shin bands;
a plurality of motion actuators, each motion actuator configured to be connected to one of the plurality of adjustable brace straps;
a plurality of sensors, each sensor connected to one of the plurality of the motion actuators, wherein each sensor is configured to measure an orientation of a corresponding adjustable brace strap and generate a motion signal;
a computing device having a circuitry including a communications device, and program instructions stored therein that, when executed by one or more processors, cause the one or more processors to:
receive the motion signals from the plurality of sensors;
measure a current range of motion of the thigh, the shin, and the knee, based on the received motion signals;
generate drive signals based on the measured current range of motion; and
transmit the drive signals to each of the plurality of motion actuators.

2. The smart knee brace system of claim 1, further comprising:
a memory located within the computing device, the memory configured to store a current set of physical therapy instructions;
wherein each motion actuator is a bi-directional linear actuator; and
the drive signals are configured to operate each bi-directional linear actuator to one of extend or retract in accordance with the current set of physical therapy instructions.

3. The smart knee brace system of claim 2, further comprising:
a physical therapy configuration, wherein the physical therapy configuration includes the knee brace, one or more thigh bands, one or more shin bands, one or more adjustable brace straps, and one or more motion actuators, in which:
the knee brace is configured to surround the knee, a first portion of the thigh and a second portion of the shin of the human patient;
a first subset of the one or more thigh bands surrounds the knee brace around the first portion;
a second subset of the one or more thigh bands surrounds the thigh above the first portion;
a third subset of the one or more shin bands surrounds the knee brace around the second portion;
a fourth subset of the one or more shin bands surrounds the shin below the second portion;
the one or more adjustable brace straps are attached between at least one of the first subset and the knee brace, the second subset and the knee brace, the first subset and the second subset, the third subset and the knee brace, the fourth subset and the knee brace, and the third subset and the fourth subset;
the one or more motion actuators are attached to the one or more adjustable brace straps; and
wherein the drive signals are configured to at least one of extend and retract the motion actuators in accordance with the current set of physical therapy instructions.

4. The smart knee brace system of claim 2, further comprising:
a computer application in bidirectional communication with the computing device, wherein the computer application is configured to:
receive the current range of motion from the communications device;
compare the current range of motion to an expected range of motion;
determine an effectiveness of the current set of physical therapy instructions based on the comparison;
generate a set of modified physical therapy instructions based on the determined effectiveness;
generate a modified physical therapy schedule based on the set of modified physical therapy instructions;
transmit data related to the modified physical therapy schedule to the communications device; and
notify one or more of the human patient, a caregiver, a physical therapist, and an orthopedic doctor of the modified physical therapy schedule.

5. The smart knee brace system of claim 4, further comprising:
a user device configured with the computer application, wherein the user device comprises a speaker; and
a voice actuation processor configured to generate voice signals based on the modified physical therapy schedule, wherein the voice signals are applied to the speaker to generate voice commands to inform the human patient of a contract time and a relax time.

6. The smart knee brace system of claim 5, wherein the voice signals comprise voice commands to instruct the human patient to one of:
add compression to the knee brace by wrapping a sleeve tightly or loosely around the knee brace;
add compression to the thigh band by wrapping the sleeve tightly or loosely around the thigh band; or
add compression to the shin band by wrapping the sleeve tightly or loosely around the shin band.

7. The smart knee brace system of claim 4, further comprising:
a sleeve configured to surround the knee brace;
an electronically controlled cooling coil located within the sleeve;
an electronically controlled heating element located within the sleeve;
at least one temperature sensor located within the sleeve, wherein the temperature sensor is configured to generate temperature signals;
wherein the current set of physical therapy instructions comprises temperature control instructions; and
wherein the computing device is configured to:
receive the temperature signals and the temperature control instructions;
analyze the temperature signals; and
transmit the temperature control signals to one of the electronically controlled cooling coil or the electronically controlled heating element in accordance with the temperature control instructions.

8. The smart knee brace system of claim 7, further comprising:
wherein the sleeve is further configured to compress the knee brace by wrapping tightly around the knee brace; and wherein the sleeve is further configured to maintain the heating or cooling of the knee brace based on the temperature control signals.

9. The smart knee brace system of claim 1, further comprising:
an immobilization configuration, wherein the immobilization configuration comprises the knee brace, one or more of the thigh bands, one or more of the shin bands and one or more adjustable brace straps, in which:
the knee brace is configured to surround the knee, a first portion of the thigh and a second portion of the shin of the human patient;
the one or more thigh bands surround the knee brace around the first portion;
the one or more shin bands surround the knee brace around the second portion; and
the one or more adjustable brace straps are attached between the one or more thigh bands and the knee brace, the one or more shin bands and the knee brace, and the one or more thigh bands and the one or more shin bands.

10. The smart knee brace system of claim 1, wherein the plurality of motion actuators includes at least one of a hydraulic actuator and an electronic actuator.

11. The smart knee brace system of claim 1, wherein the computing device is further configured to sense an activity of the human patient which indicates a desire to flex and/or straighten a knee joint based on a difference between the current range of motion and an expected range of motion.

12. A method for immobilizing a knee with a smart knee brace system, comprising:
wrapping a knee brace around a knee, a first portion of a thigh and a second portion of a shin of a human patient;
wrapping one or more thigh bands around the first portion;
wrapping one or more shin bands around the second portion;
attaching one or more brace straps between the one or more thigh bands and the knee brace, the one or more shin bands and the knee brace, and the one or more thigh bands and the one or more shin bands;
attaching one or more motion actuators to the one or more brace straps;
generating, by a computing device having circuitry including a communications device, a memory storing program instructions for knee immobilization, and one or more processors, configured to perform the program instructions, drive signals configured to one of extend or retract the one or more motion actuators in accordance with the program instructions for knee immobilization.

13. The method of claim 12, further comprising:
wrapping a sleeve around the knee brace, the sleeve configured with an electronically controlled cooling coil and an electronically controlled heating element;
measuring a temperature of the sleeve with a temperature sensor,
generating temperature signals; and
transmitting the temperature signals to the computing device;
performing one of:
applying a first electrical current to the electronically controlled cooling coil until a temperature of the sleeve is lowered to a first temperature in accordance with the program instructions for knee immobilization; or
applying a second electrical current to the electronically controlled heating element until the temperature of the sleeve is raised to a second temperature in accordance with the program instructions for knee immobilization.

14. The method of claim 13, further comprising:
performing, in accordance with the program instructions for the knee immobilization, one or more of:
compressing the knee brace by wrapping the sleeve tightly or loosely around the knee brace;
compressing the one or more thigh bands by wrapping the sleeve tightly or loosely around the one or more thigh bands; and
compressing the one or more shin bands by wrapping the sleeve tightly or loosely around the one or more shin bands.

15. A method of performing physical therapy with a smart knee brace system, comprising:
wrapping a knee brace around a knee, a first portion of a thigh and a second portion of a shin of a human patient;
wrapping a first subset of a plurality of thigh bands around the first portion;
wrapping a second subset of the plurality of thigh bands around the thigh above the first portion;
wrapping a third subset of a plurality of shin bands around the second portion;
wrapping a fourth subset of the plurality of shin bands around the shin below the second portion;
attaching one or more brace straps between at least one of the first subset and the knee brace, the second subset and the knee brace, the first subset and the second subset, the third subset and the knee brace, the fourth subset and the knee brace, and the third subset and the fourth subset;
attaching one or more motion actuators to the one or more brace straps;
receiving, by a computing device having circuitry including a communications device, a memory storing a current set of physical therapy instructions, and one or more processors configured to perform the current set of physical therapy instructions, motion signals from one or more sensors connected with the one or more motion actuators;
measuring a current range of motion of the thigh, the shin, and the knee;
generating drive signals;
actuating the one or more motion actuators in accordance with drive signals based on the current set of physical therapy instructions; and
transmitting data associated with the current range of motion to a computer application.

16. The method of claim 15, further comprising:
accessing, by the computing device, an expected range of motion from the current set of physical therapy instructions;
comparing, by the computing device, the current range of motion to the expected range of motion;
when the current range of motion matches the expected range of motion, generating, by the computing device, the drive signals; and
when the current range of motion is less than or greater than the expected range of motion, generating, by the computing device, a report regarding an effectiveness of a physical therapy schedule including the current set of physical therapy instructions.

17. The method of claim 16, further comprising:
receiving, by a user device configured with a native smart brace computer application in a bidirectional communication with the computing device, the current range of motion from the communications device;
comparing the current range of motion to an expected range of motion;
determining an effectiveness of the current set of physical therapy instructions;
generating a set of modified physical therapy instructions based on the determined effectiveness;
generating a modified physical therapy schedule based on the set of modified physical therapy instructions;
transmitting data related to the modified physical therapy schedule to the communications device;
updating the current set of physical therapy instructions with the set of modified physical therapy instructions; and
notifying one or more of the human patient, a caregiver, a physical therapist, and an orthopedic doctor of the modified physical therapy schedule.

18. The method of claim 17, further comprising:
generating voice signals by the user device based on one of the current physical therapy instructions and the set of modified physical therapy instructions;
applying the voice signals to a speaker of the user device to produce voice commands regarding a contract time and a relax time.

* * * * *